US012447249B2

(12) United States Patent
Carlsson et al.

(10) Patent No.: US 12,447,249 B2
(45) Date of Patent: Oct. 21, 2025

(54) DEVICE AND SYSTEM PROVIDING A MEDICAL SOLUTION AND A METHOD THEREOF

(71) Applicant: StayMed AB, Helsinborg (SE)

(72) Inventors: Per-Olov Carlsson, Hässleholm (SE); Thore Falkvall, Helsingborg (SE)

(73) Assignee: StayMed AB, Helsingborg (SE)

( * ) Notice: Subject to any disclaimer, the term of this patent is extended or adjusted under 35 U.S.C. 154(b) by 902 days.

(21) Appl. No.: 17/286,204

(22) PCT Filed: Oct. 21, 2019

(86) PCT No.: PCT/EP2019/078467
§ 371 (c)(1),
(2) Date: Apr. 16, 2021

(87) PCT Pub. No.: WO2020/088960
PCT Pub. Date: May 7, 2020

(65) Prior Publication Data

US 2021/0338911 A1 Nov. 4, 2021

(30) Foreign Application Priority Data

Oct. 19, 2018 (SE) .................................... 1851295-4

(51) Int. Cl.
*A61M 1/16* (2006.01)
*A61J 1/20* (2006.01)
*A61J 1/22* (2006.01)

(52) U.S. Cl.
CPC ........ *A61M 1/1666* (2014.02); *A61M 1/1654* (2013.01); *A61M 1/1656* (2013.01); *A61M 1/1668* (2014.02); *A61M 1/1694* (2013.01)

(58) Field of Classification Search
CPC .............. A61M 1/1666; A61M 1/1654; A61M 1/1656; A61M 1/1668; A61M 1/1694; A61J 1/2062; A61J 1/22; A61J 1/2089
See application file for complete search history.

(56) References Cited

U.S. PATENT DOCUMENTS 6,149,294 A 11/2000 Jonsson et al.
9,914,100 B2 3/2018 Dumschat
(Continued)

FOREIGN PATENT DOCUMENTS

EP 2035059 A2 3/2009
EP 2696910 A1 2/2014
(Continued)

OTHER PUBLICATIONS

International Search Report issued in PCT/EP2019/078467 dated Jul. 6, 2020.

*Primary Examiner* — John Kim
(74) *Attorney, Agent, or Firm* — Veros Legal Solutions LLP

(57) ABSTRACT

A device and method for providing a medical solution is described. The device comprises a first chamber adapted to have a defined volume, the first chamber is configured to be connected to a liquid providing system to fill the first chamber with the defined volume of liquid. A connector for connecting a container including at least one powder; the connector has an inlet and an outlet. A channel connecting the first chamber with the inlet of the connector, and an outlet for distributing the medical solution. The device is configured to mix the at least one powder with the defined volume of liquid for a period of time, and wherein the device is configured to fill the first chamber with the liquid from the liquid providing system while mixing the medical solution and/or distributing the mixed medical solution through the outlet.

7 Claims, 22 Drawing Sheets

(56) References Cited

U.S. PATENT DOCUMENTS

| | | | |
|---|---|---|---|
| 2015/0265760 | A1 | 9/2015 | Wilt et al. |
| 2016/0089642 | A1 | 3/2016 | Delmotte |
| 2016/0107128 | A1 | 4/2016 | Dumschat |

FOREIGN PATENT DOCUMENTS

| | | | |
|---|---|---|---|
| JP | 2008168078 | A | 7/2008 |
| WO | 2011073274 | A1 | 6/2011 |
| WO | 2018175811 | A1 | 9/2018 |

DEVICE AND SYSTEM PROVIDING A MEDICAL SOLUTION AND A METHOD THEREOF

FIELD OF THE INVENTION

This invention pertains in general to the field of providing solutions, particularly medical solutions. More particularly the invention relates to mixing at least one powder with a solvent to provide a medical solution, such as a dialysate solution.

BACKGROUND OF THE INVENTION

U.S. Pat. No. 6,149,294 discloses an apparatus for preparation of fluids intended for medical use from powder. The apparatus comprises a container such that the water and powder can be mixed and a concentrate provided in the container, and a recirculation circuit for recirculation of the water or concentrate solution into the container for further mixing of the water and powder to prepare a concentrate having a predetermined concentration.

This apparatus is able to prepare a ready mixed dialysis solution or replacement solution to be delivered to a dialysis machine performing hemodialysis (HD), hemodiafiltration (HDF) or hemofiltration (HD). The prepared solution may as well be used for other purposes, such as peritoneal dialysis, or as nutritional solution for infusion into the blood of a patient. However, this apparatus comprises several valves and other devices requiring control by a computer. Thus, there is a need for a simpler device for preparing a medical solution.

EP2035059 discloses a container comprising a plurality of compartments separated by compartment dividers, and an inlet connector for receiving a liquid via a connection tube. The compartment dividers rupture when a sufficient pressure is applied by a liquid or gas introduced into the container through the inlet connector. Some of the compartments comprise powder, which dissolves at the introduction of liquid into the container. The document further discloses a mixing system to be used with the described containers. However, there may exist a substantial time delay when preparing a new container with a ready to use solution after start of mixing the container contents with a liquid. This process can be time consuming as clean water facilities have a limited delivery amount of such water. Furthermore circulation in the bag needs to be done while a patient needs to wait for a supply of ready mixed dialysate solution.

Thus, there is a need for an improved device, system and method for mixing and providing a medical solution. It is also desired to improve the precision and quality of the final medical solution for providing to a patient. The improvement should also provide for time savings by decreasing the dissolving time and thus the effectiveness of the mixing. The device should also minimize the effect on a clinic's RO-water system. The invention may also be seen as an alternative to what is hitherto available, preferably more cost-effective.

Hence, an improved mixing system for mixing at least one powder with a solvent to provide a medical solution would be advantageous and in particular for improving the quality of a medical solution and allowing for increased flexibility and effectiveness would be advantageous.

SUMMARY OF THE INVENTION

Accordingly, examples of the present invention preferably seek to mitigate, alleviate or eliminate one or more deficiencies, disadvantages or issues in the art, such as the above-identified, singly or in any combination by providing devices and methods according to the appended patent claims.

In a first aspect of the disclosure, a device for providing a medical solution is described. The device includes a first chamber adapted to have a defined volume, the first chamber is configured to be connected to a liquid providing system to fill the first chamber with the defined volume of liquid. The device may further include a connector for connecting a container including at least one powder; the connector has an inlet and an outlet. A channel may be connecting the first chamber with the inlet of the connector. The device may further include an outlet for distributing the medical solution. The device may be configured to mix the at least one powder with the defined volume of liquid for a period of time. The device may further be configured to fill the first chamber with the liquid from the liquid providing system while mixing the medical solution and/or distributing the mixed medical solution through the outlet.

In some examples, the device may include a re-circulation pump for mixing the powder and liquid by recirculation.

In some example, the device may include a second chamber adapted to have a volume larger than the first chamber, wherein the second chamber comprises an inlet and an outlet. The inlet of the second chamber is connected to the outlet of the connector for transferring a mixture including the at least one powder and the volume of liquid from the container to the second chamber. The outlet of the second chamber may further be connected to the outlet for distributing the medical solution. The second chamber may be configured for mixing the mixture for the period of time by recirculation through the inlet and the outlet of the second chamber.

In some example, the device may include a second chamber, wherein the second chamber comprises an inlet and an outlet; the inlet of the second chamber may be connected to the outlet of the connector for transferring a mixture including the at least one powder and the volume of liquid from the container to the second chamber. The outlet of the second chamber may be connected to the outlet for distributing the medical solution. The first chamber and the second chamber may be separated by a flexible or movable wall. The second chamber may further be configured for mixing the mixture for the period of time by recirculation rough the inlet and the outlet of the second chamber.

In some examples of the device, the second chamber may include two parts, a first part and a second part, the first part has the same volume as the first chamber and may be defined by the flexible or movable wall and a fixed wall being perforated. The second part may be connected to the perforated wall to provide a larger volume to the second chamber compared to the first chamber.

In a further aspect of the disclosure, a dialysis machine which comprises a mixing device as described herein id disclosed for providing an A-concentrate.

Also, in a further aspect of the disclosure, a method of providing a medical solution is disclosed; The method includes, filling a first chamber having a defined volume with a liquid to obtain a defined volume of liquid. The method may further include connecting a container including at least one powder to a connector having and inlet and an outlet and introducing the liquid from the first chamber to the container through the inlet of the connector. The method may further include mixing the at least one powder with the defined volume of liquid for a period of time by recirculation, and distributing the medical solution through a distribution outlet. The first chamber may be filled with liquid while mixing the medical solution and/or distributing the mixed medical solution through the distribution outlet.

In one example, the method may include pumping a mixture which includes the at least one powder and the defined volume of liquid from the container to a second chamber, through the outlet of the connector to an inlet of the second chamber. Then mixing the mixture for the period of time by recirculation the mixture through the inlet and the outlet of the second chamber. The example may further include connecting the outlet of the second chamber to the distribution outlet.

In one example of the method, the medical solution may be an A-concentrate. The distribution outlet may be connected to a dialysis machine.

In another aspect of the disclosure, a method of rinsing a system for providing a medical solution is described. The method may include by-passing a connector for connecting a container, filling a first chamber having a defined volume with a liquid, and emptying the first chamber by pumping the liquid from the first chamber through the by-passed connector and through an inlet to a second chamber. The method may further include recirculating the liquid through an outlet and the inlet of the second chamber, when the first chamber is empty, for a period of time. The method may also include emptying the liquid through an outlet to a drain.

In yet another aspect of the invention, a dialysis machine having a first chamber being a buffer chamber for liquid is described. The buffer chamber having a volume, and the buffer chamber may be arranged to fill with the defined volume of the liquid up to maximum of the buffer chamber volume, such as from a liquid providing system. The machine may be controlled to distribute a mixed medical solution from the machine from a delivery chamber different than the buffer chamber, which delivery chamber previously has been in fluid communication with the buffer chamber for mixing the medical solution with liquid from the buffer chamber.

IN another aspect of the disclosure, a method of mixing a medical solution in a dialysis machine is described. The method including filling a first chamber of the machine, the first chamber being a buffer chamber, with a defined volume of liquid, while the machine may distributing a mixed medical solution from the machine from a delivery chamber different than the buffer chamber, and wherein the method may include previously mixing the medical solution in the delivery chamber with liquid from the buffer chamber.

Further embodiments of the invention are defined in the dependent claims, wherein features for the second and subsequent aspects of the invention are as for the first aspect mutatis mutandis.

It should be emphasized that the term “comprises/comprising” when used in this specification is taken to specify the presence of stated features, integers, steps or components but does not preclude the presence or addition of one or more other features, integers, steps, components or groups thereof.

BRIEF DESCRIPTION OF THE DRAWINGS

These and other aspects, features and advantages of which examples of the disclosure are capable of will be apparent and elucidated from the following description of examples of the present disclosure, reference being made to the accompanying drawings, in which.

DESCRIPTION OF EMBODIMENTS

Figure 1A:
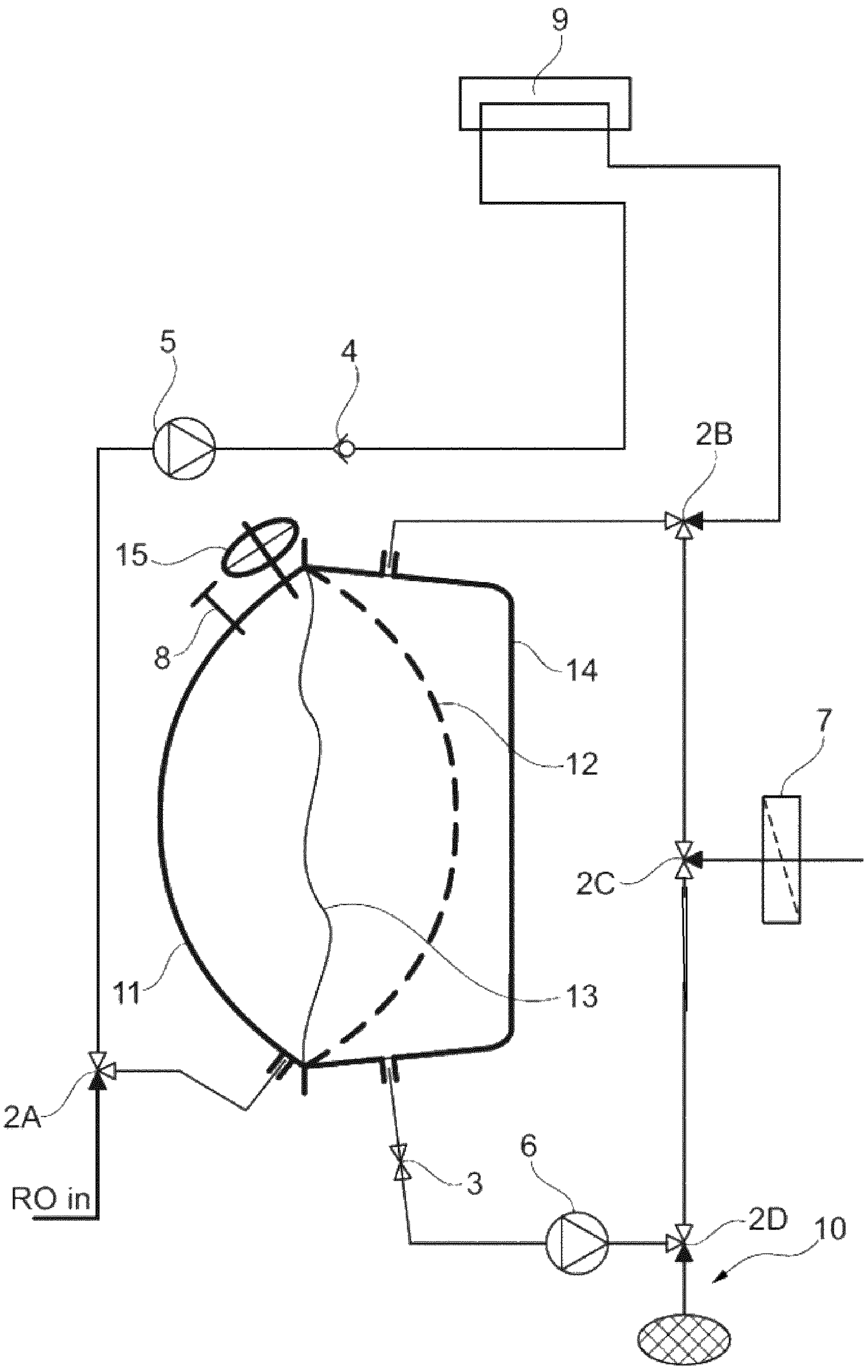
FIGS. 1A-1I are showing a schematic exemplary example of a device for providing a medical solution.

Specific examples of the disclosure will now be described with reference to the accompanying drawings. This disclosure may, however, be embodied in many different forms and should not be construed as limited to the examples set forth herein; rather, these examples are provided so that this disclosure will be thorough and complete, and will fully convey the scope of the invention to those skilled in the art.

The following description focuses on examples of the present disclosure applicable to be used with a dialysis system and in particular to the preparation of a dialysis liquid or dialysate concentrates of different concentrations using powder concentrates. However, it will be appreciated that the disclosure is not limited to this application but may be applied to many other examples of systems where it may be an advantage to provide powders to be mixed with a solvent, such as a liquid to be used with, for example, a solution providing system. Thus, medical solutions prepared by the exemplary embodiments described below may be used in dialysis treatments, as concentrate solutions or ready-made solutions for dialysis, as infusion solutions, such as Ringer’s lactate, as nutrition solutions, as replacement solutions, as plasma expander solutions, etc.

In its most general form, the device may be used for providing a medical solution by mixing at least one powder with a solvent. The medical solution may in some examples be an A-concentrate to be used in dialysis. The A-concentration may be made from a salt concentrate which together with bicarbonate is mixed with RO-water (reversed osmosis). The A-concentrate is the dialysate solution which is consumed during a renal treatment.

The system includes a disposable container, such as a bag or cartridge. The container includes at least one powder. In the example given here for dialysis, the container includes a salt, such as sodium chloride, and electrolytes, such as calcium, potassium, and magnesium. The container may also include an acid, such as acetic acid or citric acid, and glucose. The acid is commonly a solution but there are acids that are available as powders on the marked today that may be used, such as citric acid. Commonly, the container includes three separated chambers, one for the salt and the electrolytes, one for the acid and one for the glucose. The container may also be configured to have two chambers, or only one chamber, in the case the acid is provided as a powder and does not react with the other compounds or substances.

The device, which can be considered as a mixer, is positioned close to a solvent source, for example a Reverse osmosis water supply (RO-water system) used of provided a concentrate for dialysis. If the device is used with a dialysis machine, the device is arranged either close to or on the dialysis machine, for example as a stand-alone unit. Alternatively, the device may be built into a dialysis machine. In a further alternative, the device is sized to be used for central delivery at a clinic.

The device is measuring up an exact volume of solvent, for example water, this may be done for example by pumping the water into a first chamber of the system having a defined volume.

The first chamber may be fluidly connected to the inlet of a connector for connecting a container, for example by tubes. The measured solvent is then pumped to a connected container.

The solvent will mix with the powder and may be either pumped out through an outlet of the connector or may flow out by itself. The container may for example be hanged on a stand with the interface of the container to be connected to the connector of the mixing device arranged at the bottom of the container. In this arrangement, the solvent may be pumped into the container but the initial mixture between the content of the container and the solvent may flow out through an outlet of the connector without the need of a pump, alternatively a pump may be used. Alternatively, the connection interface is arranged at the top of the container, then the solvent will be pumped into the container, but the initial mix needs to be pumped out from the container, this may be done by pressurizing the container or by suction using, for example, a tube arranged as a straw inside the container.

The outlet of the connector may be connected to the device for mixing the content of the container with the solvent through recirculation using a pump, such as a circulation pump. The recirculation may be done using flow channels inside the mixing device, such as tubes, and the container. Optionally, the outlet of the connector may be connected to an inlet of a second chamber of the device, where the second chamber may be used for mixing the medical solution. The mixing may be conducted by using a pump, such as a circulation pump, for recirculating the mixture of the content of the container and the solvent, for example by recirculating the mixture out from the second chamber through an outlet thereof and back in through the inlet of the second chamber.

The recirculation of the mixture may be done for a pre-defined period of time known to achieve a complete saturation between the solvent and the content of the container. For a normal batch of A-concentrate used for a dialysis patient, the recirculation may be carried out for about 3 min. The predefined time may for example be between 1 to 10 min, 2 to 10 min, 3 to 10 min, 4 to 10 min, 5 to 10 min, 6 to 10 min, 5 to 9 min, 4 to 9 min, 3 to 9 min, 2 to 9 min, 1 to 9 min, 5 to 8 min, 4 to 8 min, 3 to 8 min, 2 to 8 min, 1 to 8 min, 5 to 7 min, 4 to 7 min, 3 to 7 min, 2 to 7 min, 1 to 7 min, 4 to 6 min, 3 to 6 min, 2 to 6 min, 1 to 6 min, 3 to 5 min, 2 to 5 min, 1 to 5 min, 2 to 4 min, 1 to 4 min, 1 to 5 min. Depending on the size of the final volume, the re-circulation has to be run for longer, such as about 15 min, such as about 20 min, such as about 30 min or longer. The recirculation may also be run until a completely saturated solution between the solvent and the content of the container has been achieved.

When the mixing has been finalized the medical solution is distributed through and outlet of the mixing device. The medical solution may either be pumped out from the mixing device or suction from an external device may be used. The outlet may for example be connected to a dialysis machine, for example by connecting the device to the connection for "central delivery system".

Depending on how the mixing device is arranged, the first chamber, such as the measuring chamber, may start to fill up with a solvent either during the recirculation or when the distribution of the medical solution starts. A new container may be connected to the device after the first one has been emptied, for example when the recirculation starts or during distribution of the finished medical solution. Alternatively, the container may also be attached to the device as soon at the distribution of the previous batch of medical solution has been distributed.

Since the solvent, such as water from the RO-water system, has been measured during the recirculation or distribution of the previous batch, the mixing may start direct when the distribution has finished. This allows for a new batch of medical solution to be prepared and started to be distributed within the time for the re-circulation, i.e. for a dialysis patient around 3 min.

An advantage is that the volume of solvent will always be the exactly the same, while the content of the container may be varied, for example, when preparing an A-concentrate, with respect to the amount of salt, electrolytes, acid or glucose to provide a specific recipe or formula being prescribed.

Another advantage is that each container may include ingredients that has been weighted up separately with high accuracy, each container may therefore be a batch with a specific recipe or formula.

A further advantage of this arrangement, is that the system allows a longer filling time of solvent. Demanding all the solvent, such as RO-water, needed for the preparation immediately under a short period of time, may cause a high load on a supply system, for example a RO-water supply system. Even about 2 lite of RO-water, which is the normal volume required for a single batch, may cause a too high load if the mixing device must be filled under a short period of time. In a standard RO system, only about 500 ml/min is what maximum can be supplied to II outlets. A high load on a supply system, such as a RO-water supply system, may cause disturbances or in worse case break down the system, so that all units in a clinic may not receive the amount of water they require, which may cause problems for other departments or patents not receiving any water when needed. This may further prolong the preparation of a batch. With the system described herein, the withdrawal of RO-water may be around 15 ml/min if the system is filled up with the same rate as final medicament is being delivered to the patient. In some examples of the system, even lower amount of RO-water may be withdrawn if a first chamber used for measuring the volume may be filled during both mixing and delivery of a different batch.

FIGS. 1A to 1I are illustrating a schematic example of a mixing device according to the disclosure. With reference to FIG. 1A, the system includes a tank divided into two parts separated by a flexible wall or movable wall 13, for example an elastic membrane. One part is the first chamber 11, and the other part is the second chamber 12. In one example, when the tank is empty, both chambers have the same shape. The first chamber 11 having a defined volume for measuring a volume of a liquid, such as a solvent, such as water. The first chamber 11 is connectable through an inlet to a liquid supply, such as a RO-water supply system. The first chamber 11 may include sensor 8, such as a pressure transmitter or pressure sensor. The first chamber 11 may also include a vent 15, such as a breather.

The second chamber 12 may comprise a wall which is perforated, like a strainer. The second chamber, further comprises an inlet for receiving unsolved solution from the container, and an outlet used for recirculating the solution during mixing. The outlet of the second chamber 2 is also used during distribution of the finished solution and when draining the system during cleaning.

The second chamber 12 may also include an extension 14, such as a housing, connected to and covering the perforated wall. The extension 14 provides extra volume to the second chamber 12 needed since the solution has a larger volume than the measured volume of solvent introduced to the first chamber 11 due to the volume of the content of the solution should be mixed with.

The device may further include some valves, for example, 2A, 2B, 2C, 2D, and 3. The device may also include a valve 4 to prevent back flow.

Valve 2A is configured for allowing solvent to flow into the first chamber 11 from the supply, such as a RO-water supply system. The flexible or movable wall 13 is pushed into the second chamber 12. The air in the first chamber may exit through the vent 15. When filling the first chamber 11 with a solvent, the flexible or movable wall 13 may reach an inside of the perforated wall, due to the pressure of the solvent. When the first chamber 11 is filled with solvent, the pressure will increase inside the first chamber 11 whereby the sensor 8 may send a signal to close the valve 2A which stops the filling of the first chamber 11. In this way, the volume of solvent, such as water, will be the same each time when starting the mixture.

A valve, such as valve 2A may be configured to open to allow the solvent to flow out from the first chamber 11 and to the inlet of a connector 9. Emptying the first chamber 11 may be aided by using pump 5. The solvent will be mixed with the content of a container connected to the connector 9. The container includes at least one powder which will be dissolved in the solvent. The mixed flows out from an outlet of the connector 9 via valve 2B to an inlet of the second chamber 12 and the extension 14.

After the first chamber 11 and the container has been emptied, valve 2B closes the connection to the outlet of the connector 9 and the mixing device is adjusted to facilitate the recirculation of the at least partially unsolved mixture of the at least one powder and the solvent, for example by opening valves 3, 2C and 2D. Pump 6 is then starting to re-circulate the mixture from an outlet of the second chamber 12 and through a tube system back to an inlet of the second chamber 12. The recirculation is carried out until a completely saturated solution is obtained from the mixture of solvent and the at least one powder. The finished medical solvent is then distributed through outlet 7, for example via valve 2C. When the finished solution is an A-concentrate for dialysis, the outlet 7 may be connected to an inlet for "Central Delivery System" on the dialysis machine.

The device may also be connectable to a drain when draining and cleaning the mixing system, for example via valve 2D.

The mixing device may include, apart from the chambers, pumps, valves tubes and connectors, also the electronics used for regulating the process and the different sequences of the mixing process. When the mixing device is configured as a stand-alone machine, the mixing device may also include a display for displaying, for example, start, stop, and the present sequence being carried out. The device may also have an input unit, such as a keyboard or a touch screen.

Some of the Different Modes that the Device May be Perform are:

FIG. 1A is illustrating an example of a standby mode. In this mode, the device is empty and does not include any solvent or finished solution, such as A-concentrate. The device is connected to a solvent supply, such as a water supply, such as RO-water. Valve 2A is in this mode closed. The device may be connected to a machine to which is it distributing the obtainer medical solution, such as connection for delivering A-concentrate on a dialysis machine. Further, the device may be connected to a drain.

Figure 1B:
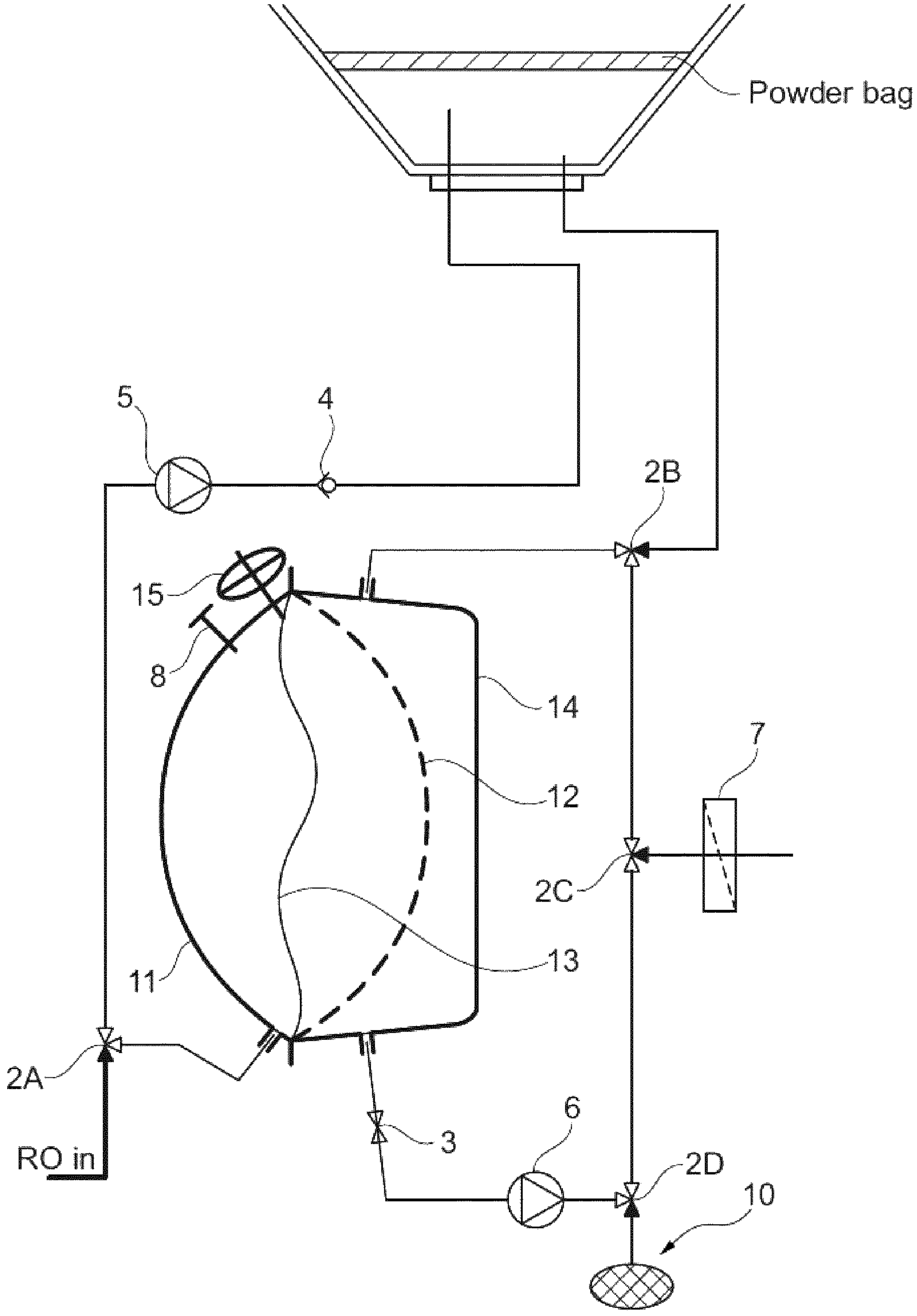

FIG. 1B is illustrating an example of a mode of connecting a container. In this mode, a container, such as a bag or cartridge, is connected to the connector 9. When connecting the container to the device, the container may for example be hanged on a stand with the interface of the container to be connected to the connector of the mixing device located at the bottom of the container. Alternatively, the connection interface is arranged at the top of the container, then the solvent may be pumped into the container, but the initial mix of partially unsolved mixture of the at least one powder and the solvent needs to be pumped out from the container, this may be done by pressurizing the container or by suction using, for example, a tube arranged as a straw inside the container.

The disclosure is not limited to a specific type of connector or container. In this application, an example of a connector and container is disclosed, but other connectors and containers known in the art would work, for example, connectors and containers described in EP2723417, EP2035059, and U.S. Pat. No. 6,149,294. Neither is the disclosure limited to a single container. The system may be adapted so that, for example, two, or three separate containers are connected to the mixing device. For example, where the powders are in a first container, and the acid in a second container; or where the salt and electrolyte is arranged in a first container, the acid in a second container, and the glycose in a third container.

Figure 1C:
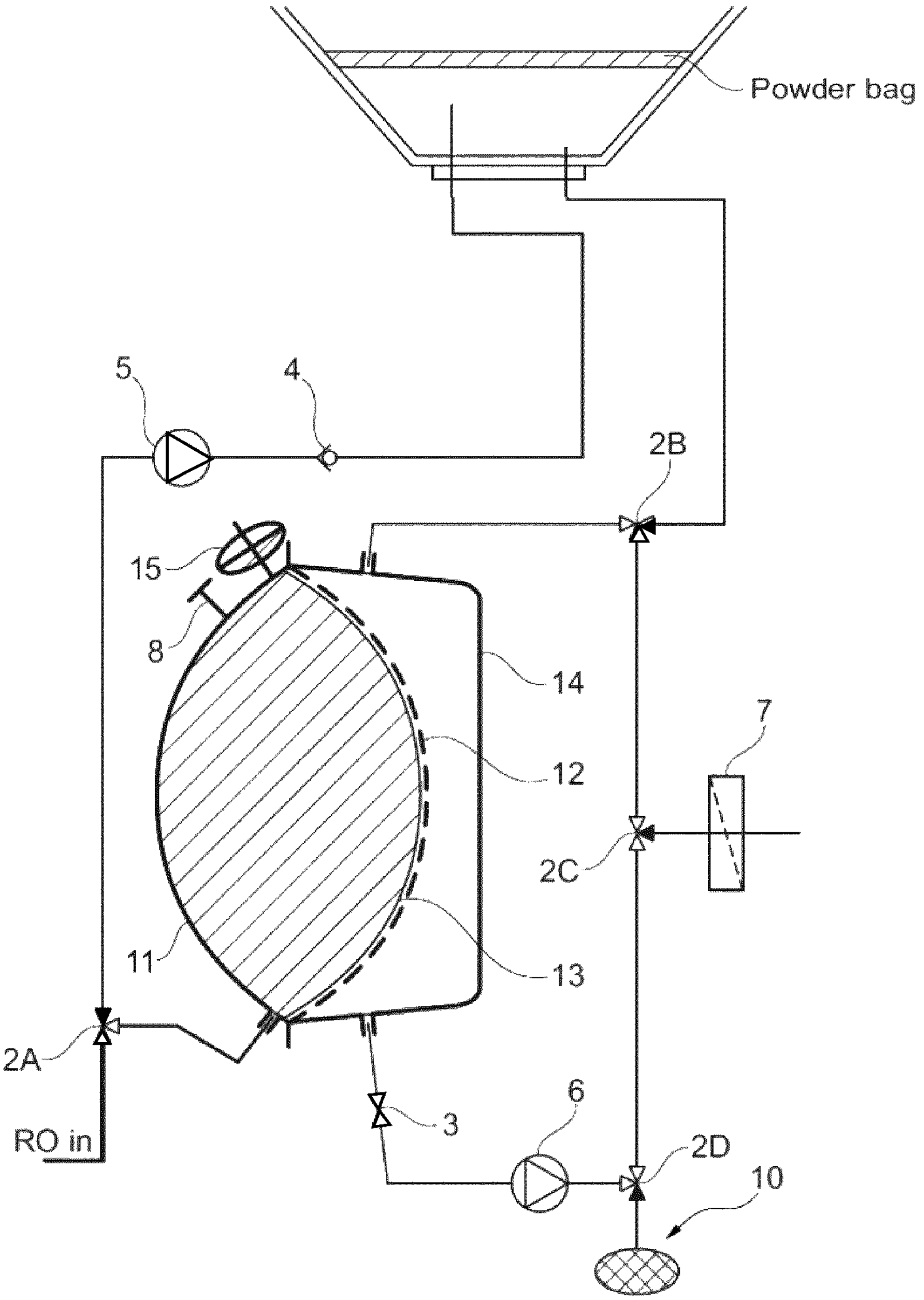

FIG. 1C is illustrating and example of a start-up mode. In this mode, the first chamber 11 is getting filled up with a solvent, such as RO-water, by opening valve 2A. The start-up mode may be initiated by a confirmation, for example, by pushing a button or touching an area on the display. The first chamber 11 is filled until sensor 8 indicates that the first chamber 11 is completely filled with solvent, and whereby valve 2A closes.

When filing the first chamber 11 with a solvent, the flexible or movable wall 13 is pushed into the second chamber 12. The air in the first chamber may exit through the vent 15. When filling the first chamber 11, the flexible or movable wall 13 reaches an inside of the perforated wall, due to the pressure of the solvent. When the first chamber 11 is filled with solvent, the pressure will increase inside the first chamber 11 whereby the sensor 8 may send a signal to close the valve 2A which stops the filling of the first chamber 11. In this way, the volume of solvent, such as water, will be the same each time when starting the mixture.

For RO-water, the first time the start-up mode is run, it may be possible to utilize up to the full rate of RO-water delivery. The reason is that the start-up mode may be done at a time of the day when there is not much demand for RO-water. For the consecutive fill-ups of water during a day a restriction to the delivery rate of mixed medicament to a patient, such as about 15 ml/min, may apply.

Figure 1D:
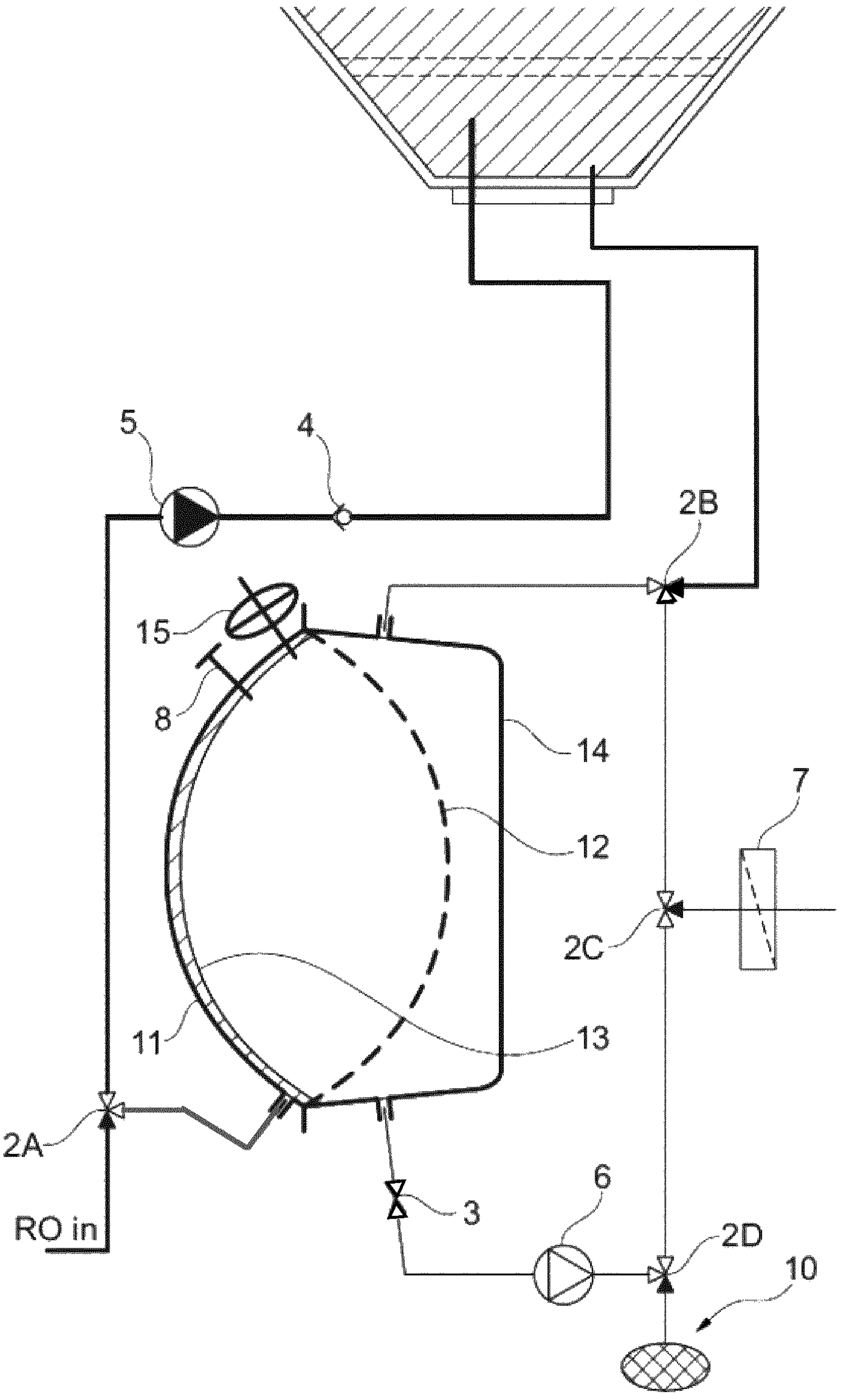

FIG. 1D is illustrating an example of a mode of filling a container. During this mode, pump 5 starts to pump, and the container starts to get filled by solvent. Depending on the type of container used, the process may vary. For example, using containers, similar to the containers described in EP2723417, and EP2035059, where there are dividers, such as welded seams, that needs to be opened-up, the outlet of the connector is closed, and a pressure is built up inside the container by the solvent. This may be done by close valve 2B. The increased pressure will break the dividers and allowing the solvent to mix with the content of the container and starting to dissolve the at least one powder therein. In other examples, where separated containers, or a single container having columns where each column is individually connected to the connector 9, are used, the solvent fills the container and start to mix with the at least one powder. The content starts to dissolve which allows the bag to be emptied.

Figure 1E:
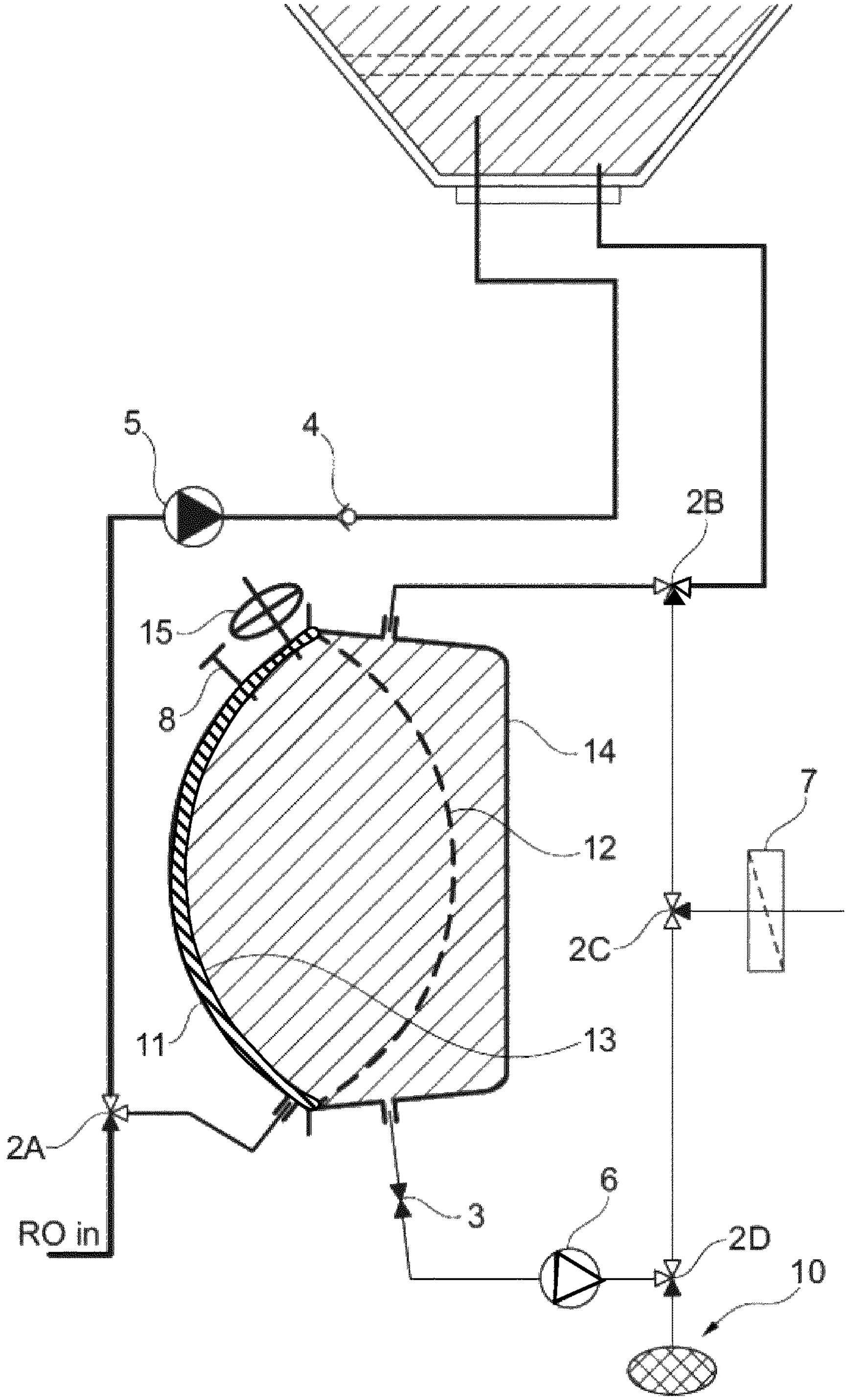

FIG. 1E is illustrating an example of a mode of emptying a container. In this mode, the content of the container is emptied to the second chamber 12 by pump 5 pumping solvent, such as water, from the first chamber 11 and through the container. Pump 5 is running until the first chamber 11 is empty. When the first chamber 11 is empty, the valve 2A and 2B may close and the container may be replaced according to the "connecting a container mode" described above, and the next "start-up" mode may also be prepared.

Figure 1F:
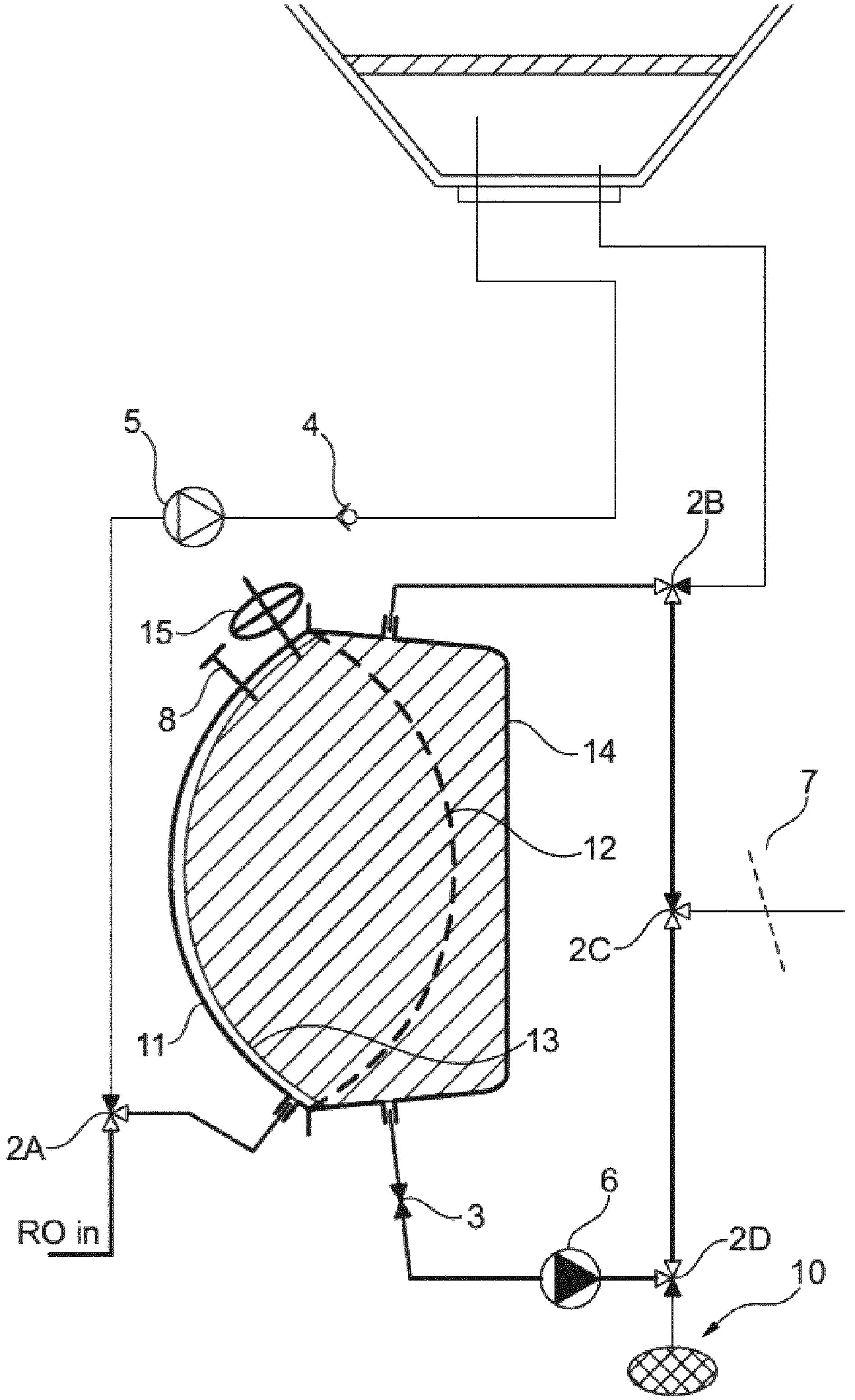

FIG. 1F is illustrating an example of a recirculation mode. When the container has been emptied and the outlet of the connector closed, pump 6, such as a recirculation pump, starts to recirculate the mixture through and inlet and an outlet of the second chamber 12, and tubes connecting them. The recirculation is performed until the mixture is completely saturated and all the powder has been dissolved. The re-circulation may be performed for a defined period of time which is calibrated so that the finished solution will be fully saturated after that defined time or recirculation.

Figure 1G:
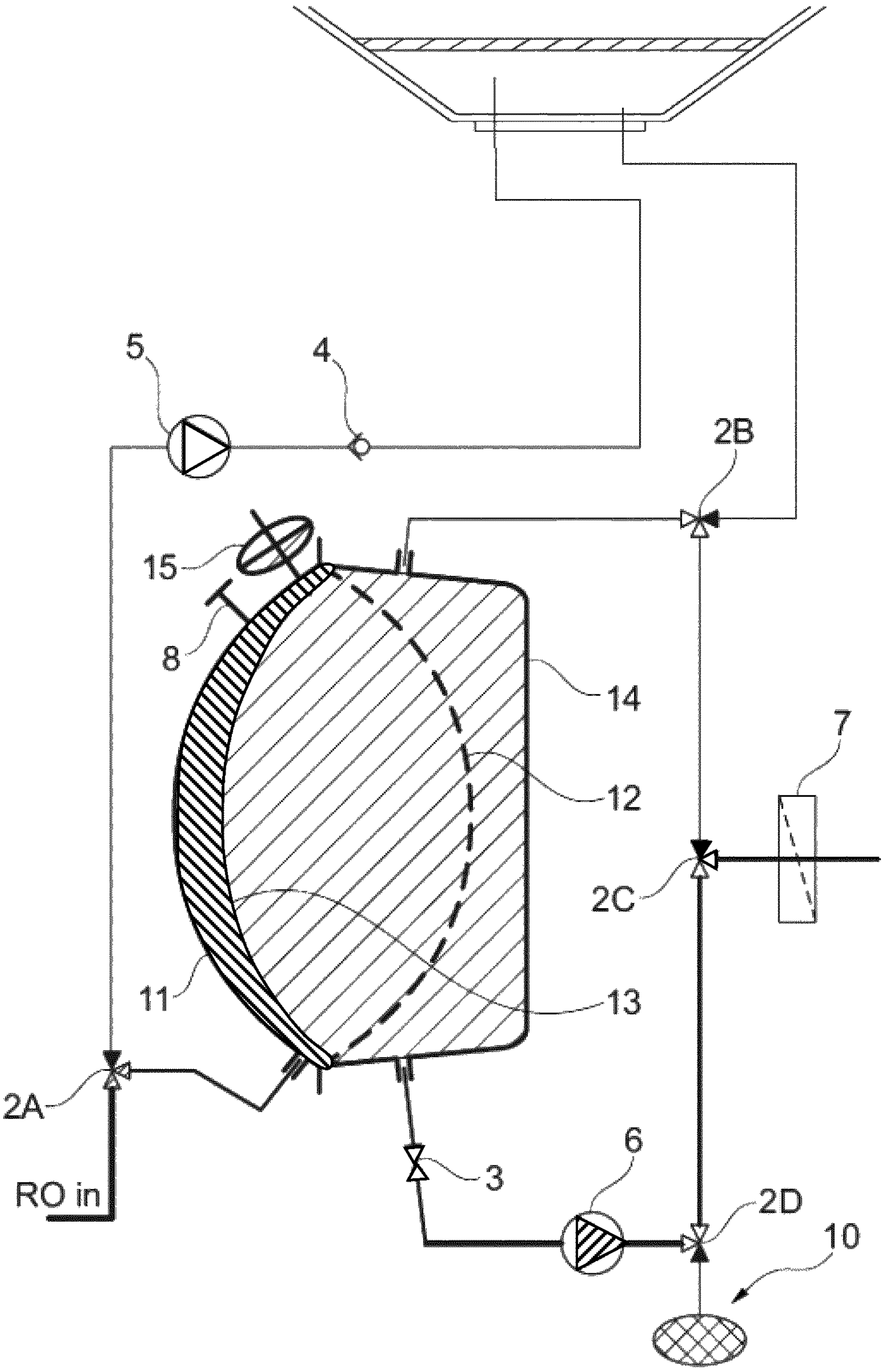

FIG. 1G is illustrating an example of a distribution mode. In this mode is the finished solution distributed, for example through valve 2C. When the finished solution starts to be distributed from the mixing device, the "start-up" mode may be initiated to start to fill the first chamber 11 with a solvent. In this example, because the first chamber 11 and the second chamber 12 are sharing the same volume due to the function of the wall 13, the filling rate of the first chamber 11 may be automatically restricted to the same rate as finished medicament is withdrawn from the second chamber 12, After the first chamber 11 has been filled, mode for filling the container may be initiated.

The advantages of this is that the machine will be ready to start to mix the solution through recirculation without first filling up the device with water. This allows for a new batch of medical solution to be prepared and started to be distributed within the time for the re-circulation, i.e. for a dialysis patient around 3 min. Another advantage of this arrangement, is that the system allows a longer filling time of solvent. Demanding all the solvent, such as RO-water, needed for the preparation immediately under a short period of time, may cause a high load on a supply system, for example a RO-water supply system. Even about 2 liters of RO-water, which is the normal volume required for a single batch, may cause a too high load if the mixing device must be filled under a short period of time. A high load on a supply system, such as a RO-water supply system, may cause disturbances or in worse case break down the system, so that all units in a clinic may not receive the amount of water they require, which may cause problems for other departments or patents not receiving any water when needed. This may further prolong the preparation of a batch.

In the example of the finished solution being an A-concentrate, the outlet of the device may be connected to a dialysis machine and the concentrate may pass through an exchangeable particle filter. The filter may be arranged in a tube connecting the mixing device with the dialysis machine. The tube may be connected to dialysis machine at the inlet for "central delivery system". There are three main ways a dialysis machine may receive the finished A-concentrate: the dialysis machine uses suction to receive the concentrate from the mixing device; the recirculation pump 6 is used to pump out the solution to the dialysis machine; and the filling of the first chamber 11 with a solvent may push out the finished solution in the second chamber 12.

Figure 1H:
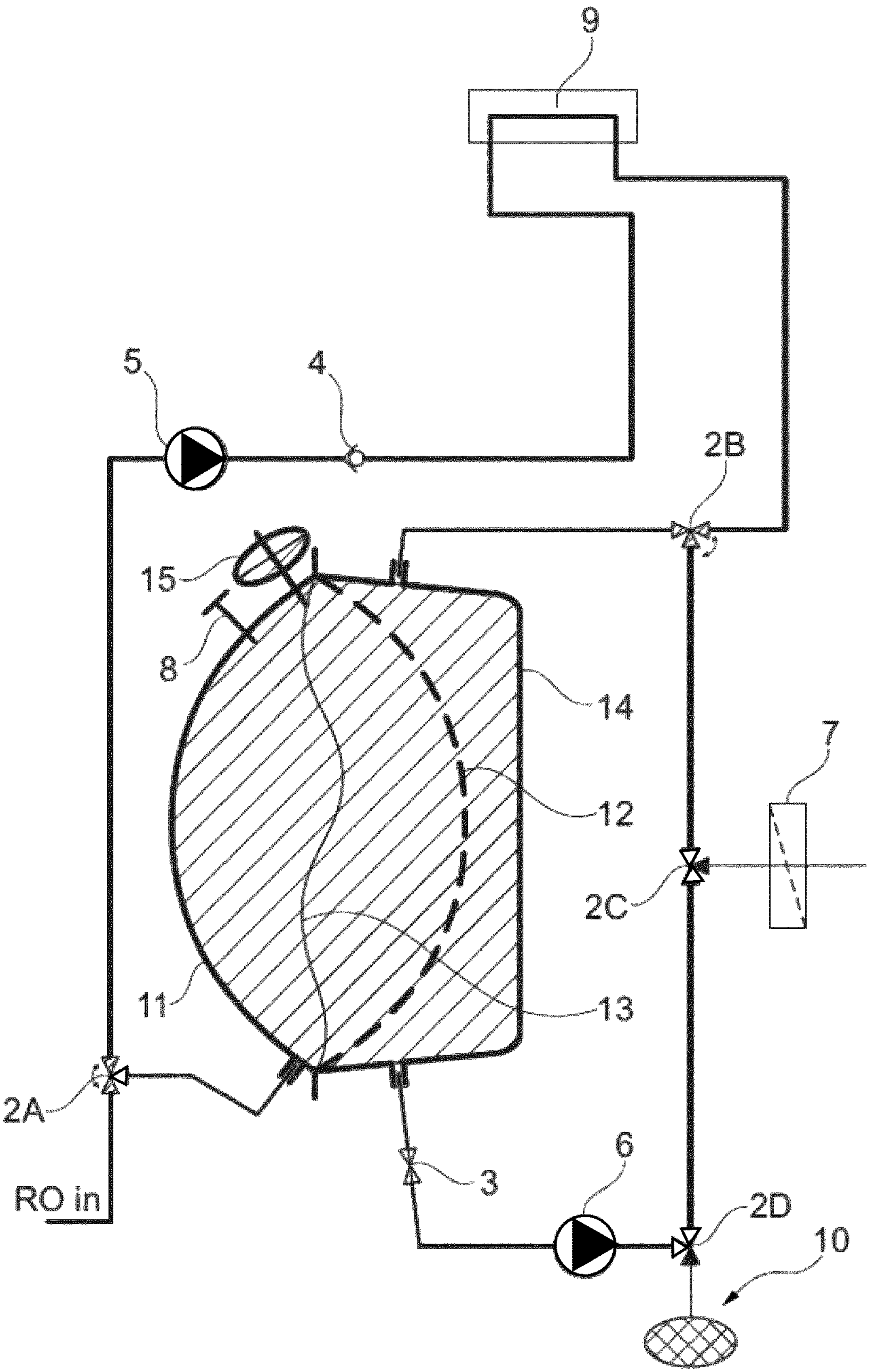

FIG. 1H is illustrating an example of a rinse mode. When the number of batches needed has been prepared, the device needs to be rinsed to remove any residuals. The connector is first arranged in a by-pass mode. How the connector is arranged in a by-pass mode depends on the connector. For some connectors, an adapter is needed to connect the inlet and the out let of the connector. In other examples, the inlet and the outlet can be directly connected to each other to provide a by-pass arrangement.

The solvent, such as RO-water, in the first chamber 11, is pumped, for example by pump 5, through the bypassed connector and into the second chamber 12. When the first chamber 11 is empty, the recirculation pump 6 starts to recirculate the solvent through the inlet and the outlet of the second chamber 12 and the tubes connecting them. This will rinse the part of the mixing device that has been in contact with the solution and will flush out any residuals of the solvent.

A-concentrate is considered to be sterile and it is therefore not required during normal use to rinse the system with more than RO-water. Sometimes disinfection may be needed, for example if the system may have been exposed to any risk for contamination. For example, if the device has been serviced or repaired; or if not used for a long time. Disinfection may also be needed if the disclosed technology is used for mixing a solution that is not sterile. The device may be disinfected by connecting a container with a disinfecting solution or powder and then mix it and recirculating the solution in the device before being drained. Alternatively, the inlet may be connected to source of disinfecting solution which is pumped in and recirculated in the device before being drained.

After the device has been disinfected a rinse mode may be run to remove any residuals of the disinfection solution.

Figure 1I:
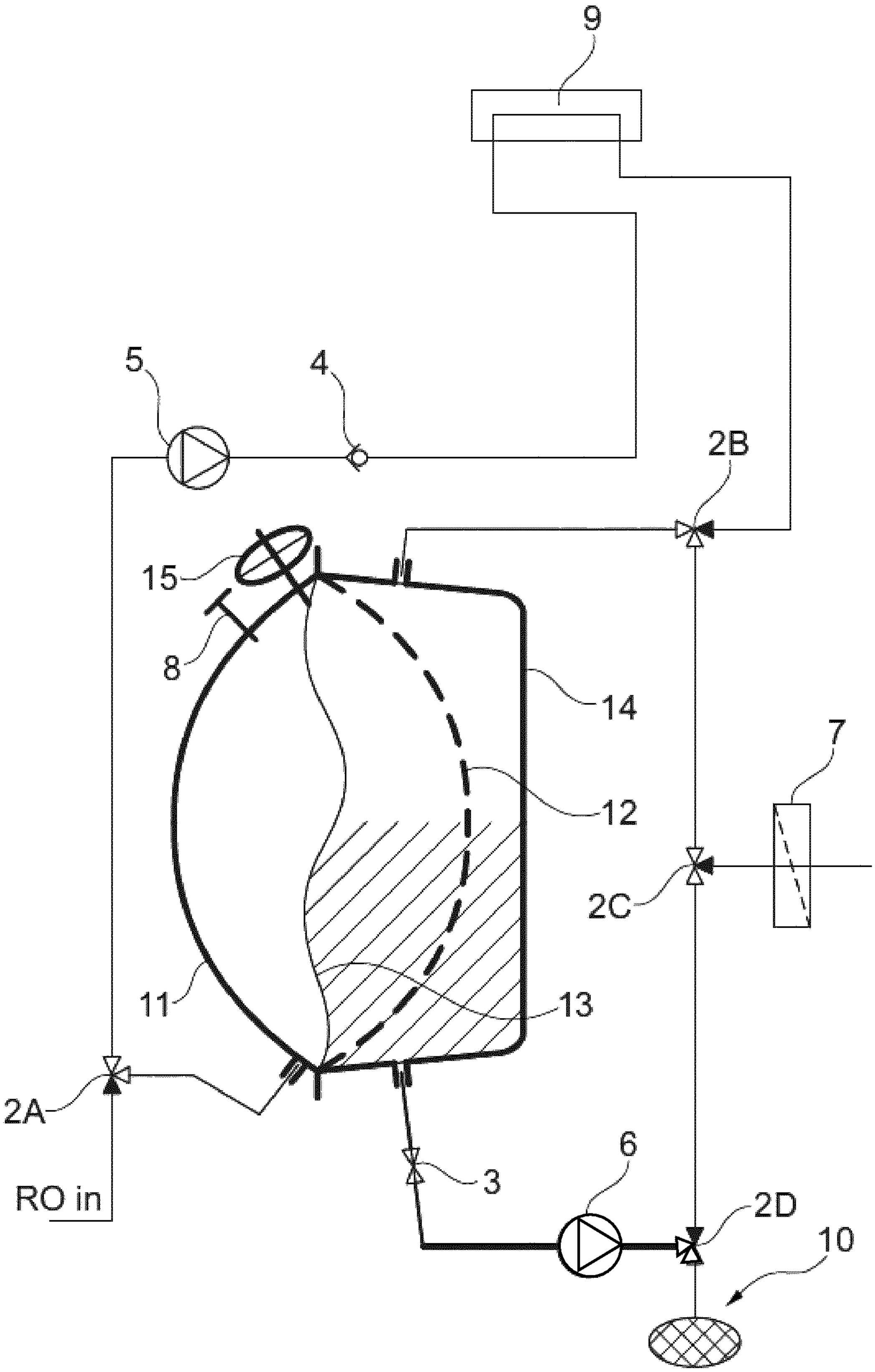

FIG. 1I is illustrating an example of a drain mode. When the device has been rinsed, the solvent used for rinsing the device is emptied into a drain, such as by open valve 2D.

The rinse mode and drain mode may be repeated should so be needed. A special rinsing liquid may also be used for this process.

Figure 2A:
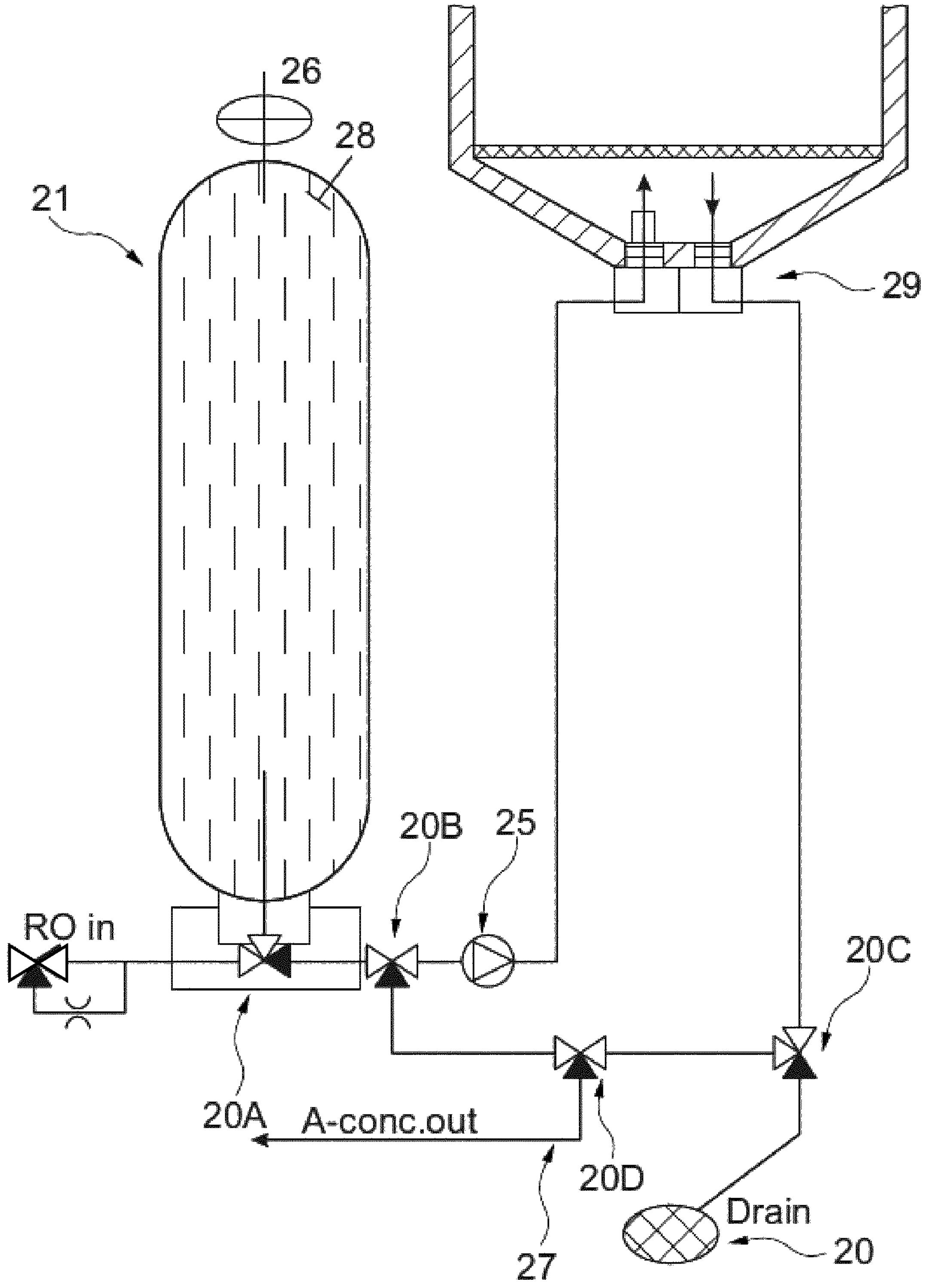
FIGS. 2A-2E are showing a schematic exemplary example of a device for providing a medical solution.

FIGS. 2A to 2E are illustrating a schematic example of a mixing device according to the disclosure. With reference to FIG. 2A, the device includes first chamber 21. The first chamber 21 having a defined volume for measuring a volume of a liquid, such as a solvent, such as water. The first chamber 21 is connectable through an inlet to a liquid supply, such as a RO-water supply system. The first chamber 21 may include sensor 28, such as a pressure transmitter or pressure sensor. The first chamber 21 may also include a vent 26, such as a breather.

The device may further include some valves, for example, 20A, 20B, 20C, and 20D. Valve 20A is configured for allowing solvent to flow into the first chamber 21 from the supply source, such as a RO-water supply system. When filling the first chamber 21 with a solvent, the air in the first chamber 21 may exit through the vent 26. When the first chamber 21 is filled with solvent, the pressure will increase inside the first chamber 21 whereby the sensor 28 may send a signal to close the valve 20A which stops the filling of the first chamber 21. In this way, the volume of solvent, such as RO-water, will be the same each time when starting the mixture.

Valves, such as valve 20A and 20B may be configured to open to allow the solvent to flow out from the first chamber 21 and to the inlet of a connector 29. Emptying the first chamber 21 may be aided by using pump 25. The solvent will be mixed with the content of a container connected to the connector 29. The container includes at least one powder which will be dissolved in the solvent.

After the first chamber 21 has been emptied into the container, valve 20B closes the connection between the first chamber 21 and the inlet of the connector 29. The mixture flows out from an outlet of the connector 29 via valve 20C and into a tubing system of the mixing device. the at least partially unsolved mixture of the at least one powder and the solvent is recirculated by pump 25 through the container and the tubing system of the device, for example by opening valves 20B and 20C. The recirculation is carried out until a completely saturated solution is obtained from the mixture of solvent and the at least one powder. The finished medical solvent is then distributed through outlet 27, for example via valve 20D. When the finished solution is an A-concentrate for dialysis, the outlet 27 may be connected to an inlet for "Central Delivery System" on the dialysis machine.

The device may also be connectable to a drain 20 when draining and cleaning the mixing device, for example via valve 20C.

The mixing device may include, apart from the chambers, pumps, valves tubes and connectors, also the electronics used for regulating the process and the different sequences of the mixing process. When the mixing device is configured as a stand-alone machine, the mixing device may also include a display for displaying, for example, start, stop, and the present sequence being carried out. The device may also have an input unit, such as a keyboard or a touch screen.

Some of the Different Modes that the Device May be Perform are:

FIG. 2A is illustrating an example of a mode of connecting a container and a start-up mode. Before this mode, the device may be in a stand-by mode (not illustrated) here no container is connected, and no solvent is filling-up the first chamber 21, i.e. similar to the stand-by mode illustrated in FIG. 1A.

In the mode for connecting a container, the container, such as a bag or cartridge, is connected to the connector 29. When connecting the container to the device, the container may for example be hanged on a stand with the interface of the container to be connected to the connector of the mixing device located at the bottom of the container. Alternatively, the connection interface is arranged at the top of the container, then the solvent may be pumped into the container, but the initial mix of partially unsolved mixture of the at least one powder and the solvent needs to be pumped out from the container, this may be done by pressurizing the container or by suction using, for example, a tube arranged as a straw inside the container.

The disclosure is not limited to a specific type of connector or container. In this application, an example of a connector and container is disclosed, but other connectors and containers known in the art would work, for example, connectors and containers described in EP2723417, EP2035059, and U.S. Pat. No. 6,149,294. Neither is the disclosure limited to a single container. The system may be adapted so that, for example, two, or three separate containers are connected to the mixing device. For example, where the powders are in a first container, and the acid in a second container; or where the salt and electrolyte is arranged in a first container, the acid in a second container, and the glycose in a third container.

In the start-up mode, the first chamber 21 is getting filled up with a solvent, such as RO-water, by opening valve 20A. The start-up mode may be initiated by a confirmation, for example, by pushing a button or touching an area on the display. The first chamber 21 is filled until sensor 28 indicates that the first chamber 21 is completely filled with solvent, and whereby valve 20A closes. In this way, the volume of solvent, such as water, will be the same each time when starting the mixture For RO-water, the first time the start-up mode is run, it may be possible to utilize up to the full rate of RO-water delivery. The reason is that the start-up mode may be done at a time of the day when there is not much demand for RO-water. For the consecutive fill-ups of water during a day a restriction to the delivery rate of mixed medicament to a patient, such as about 15 ml/min or lower, may apply.

Figure 2B:
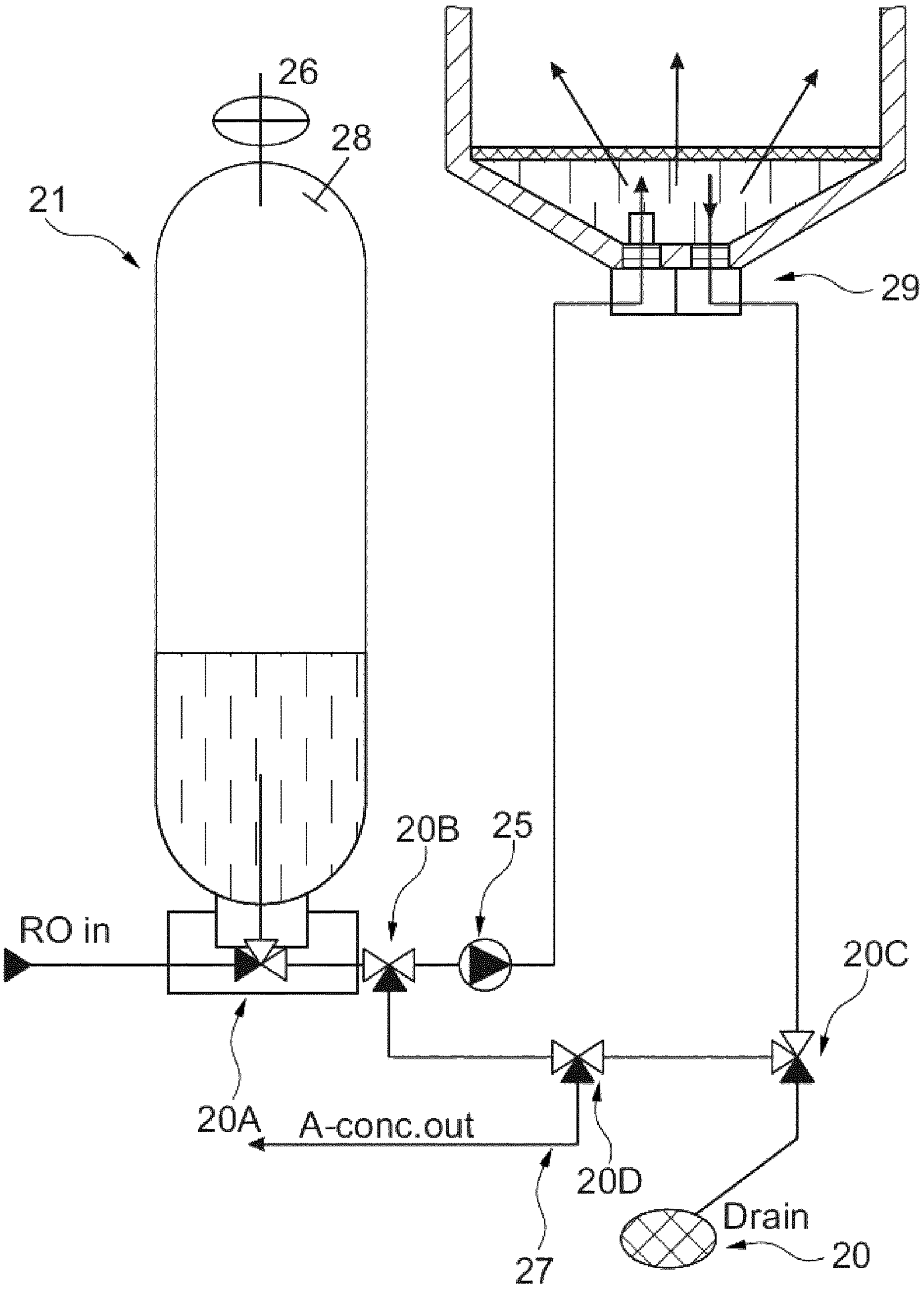

FIG. 2B is illustrating an example of a mode of filling a container. During this mode, pump 25 starts to pump, and the container starts to get filled by the solvent, such as RO-water. Depending on the type of container used, the process may vary. For example, using containers, similar to the containers described in EP2723417, and EP2035059, where there are dividers, such as welded seams, that needs to be opened-up, the outlet of the connector is closed, and a pressure is built up inside the container by the solvent. This may be done by closing valve 20B. The increased pressure will break the dividers and allowing the solvent to mix with the content of the container and starting to dissolve the at least one powder therein. In other examples, where separated containers, or a single container having columns wherein each column is individually connected to the connector 29 are used, the solvent fills the container and start to mix with the at least one powder. The content starts to dissolve which allows the bag to be emptied.

Figure 2C:
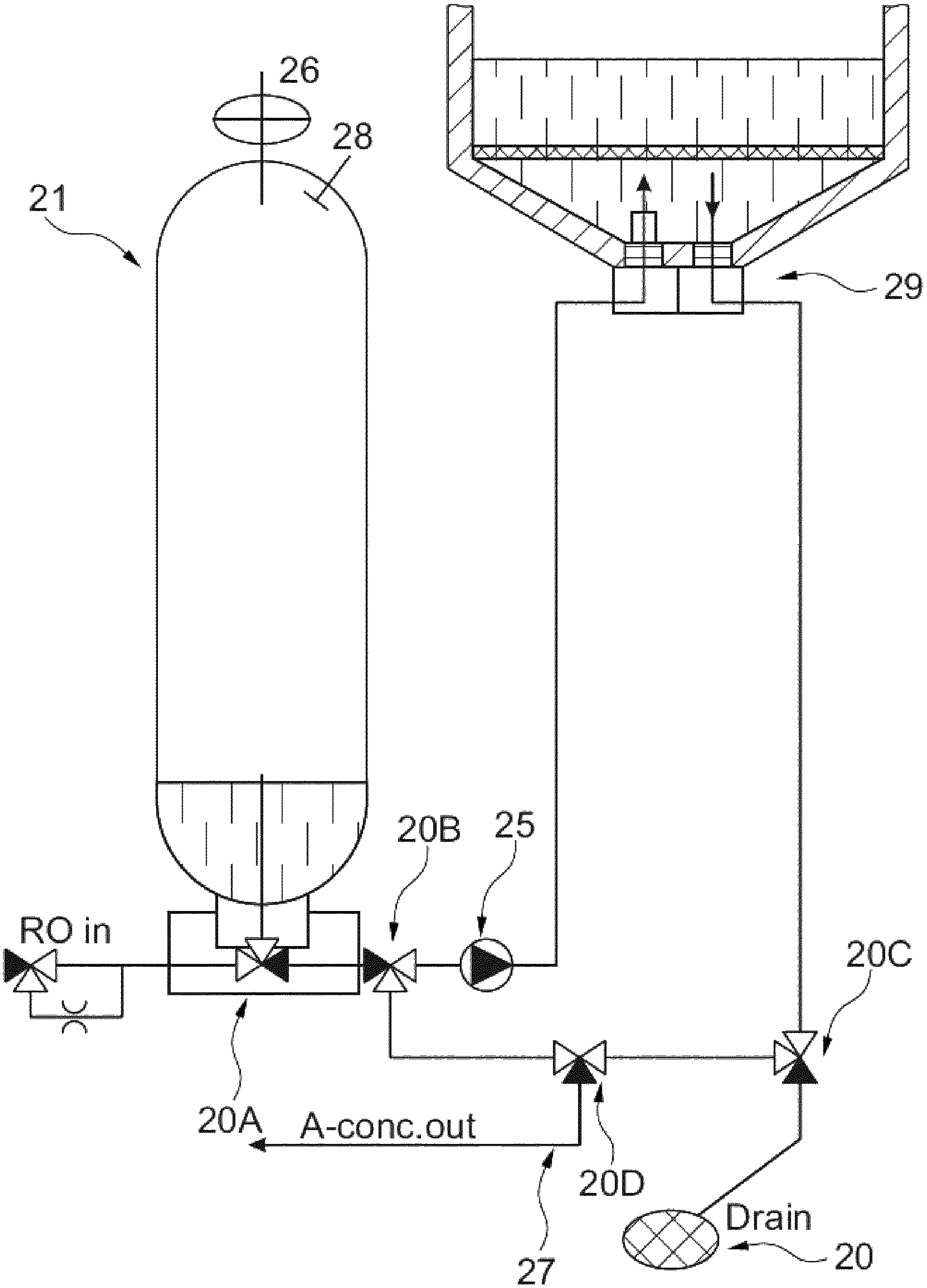

FIG. 2C is illustrating an example of a recirculation mode. When the container has been emptied and the valve 20B has closed the fluid connection between the first chamber 21 and the connector 29, pump 25 may starts to recirculate the mixture through an inlet and an outlet of the connector 29 and pumping the solution through the connected container, and tubes connecting the inlet and the outlet. The recirculation is performed until the mixture is completely saturated and all the powder has been dissolved. The re-circulation may be performed for a defined period of time which is calibrated so that the finished solution will be fully saturated after that defined time or recirculation. When the first chamber 21 is empty, and the re-circulation has started, next "start-up" mode may also be prepared by filling the first chamber 21 with a solution.

Figure 2D:
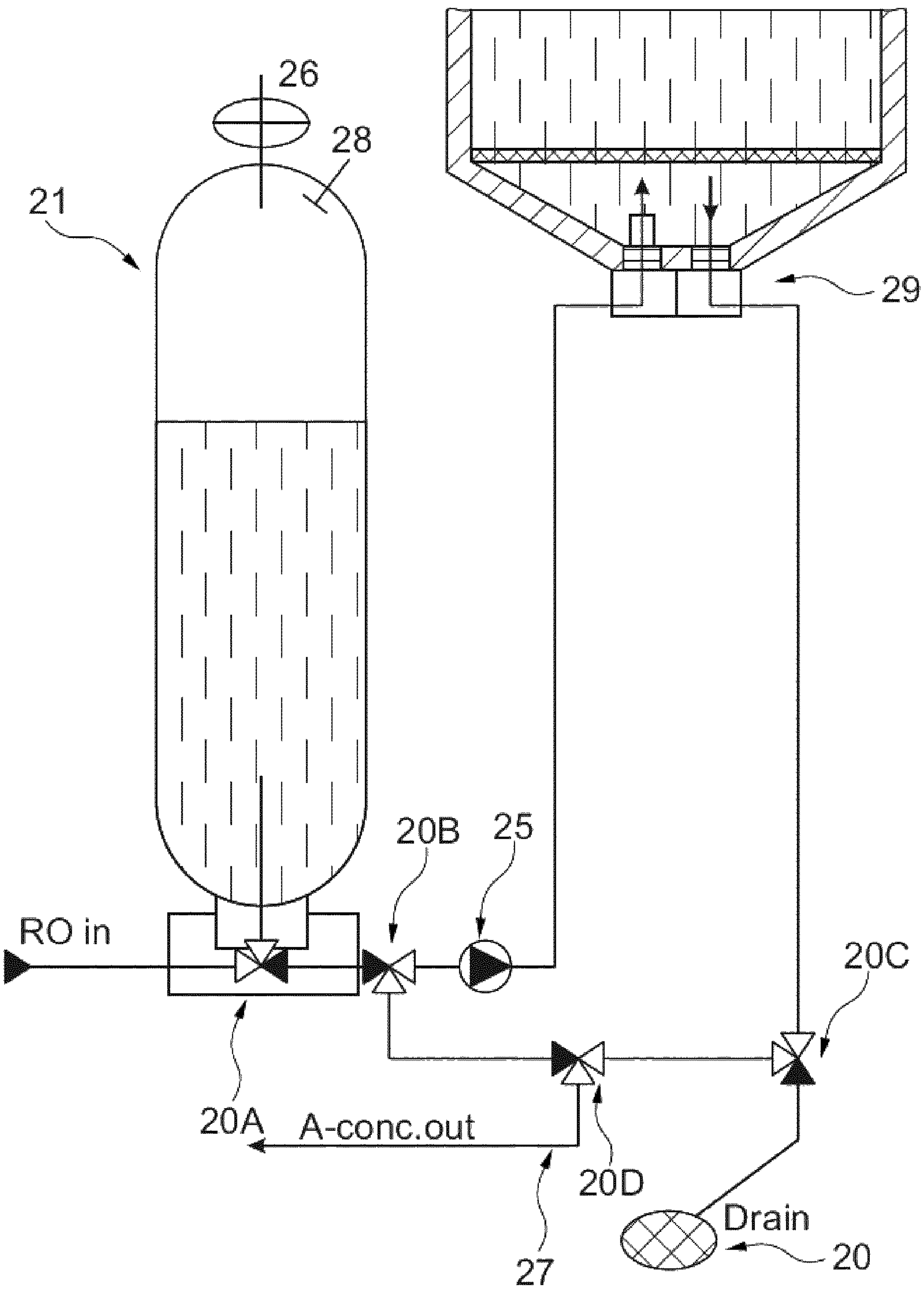

FIG. 2D is illustrating an example of a distribution mode. In this mode is the finished solution distributed, for example through valve 20D. When the finished solution starts to be distributed from the mixing device, the "start-up" mode may be initiated to start to fill the first chamber 21 with a solvent, such as RO-water. The advantages of this is that the machine will be ready to start to fill the container with a well-defined volume of water and to start to mix the solution through recirculation without first waiting for the device to be filled-up with water. This allows for a new batch of medical solution to be prepared and started to be distributed within the time for the re-circulation, i.e. for a dialysis patient around 3 min. Another advantage of this arrangement, is that the system allows a longer filling time of solvent. Demanding all the solvent, such as RO-water, needed for the preparation immediately under a short period of time, may cause a high load on a supply system, for example a RO-water supply system. Even about 2 liters, which is the normal volume required for a single batch, may cause a too high load if the mixing device must be filled under a short period of time. A high load on a supply system, such as a RO-water supply system, may cause disturbances or in worse case break down the system, so that all units in a clinic may not receive the amount of water they require, which may cause problems for other departments or patents not receiving any water when needed. This may further prolong the preparation of a batch.

If the first chamber 21 may start to get filled during the mixing of a preparation of a solution, the time it may take to fill up the first chamber 21 may be allowed to be longer than when only filing the first chamber 21 during delivery of a preparation. A longer filling time may allow a lower flow rate from a supply system, such as a lower rate than 15 ml/min which is the delivery rate of an A-concentrate to a patient. A lower flow rate decreases the risk of a too large total demand from a source of liquid, such as RO-water.

If the first chamber 21 may start to get filled during the distribution of a prepared solution, the filling time of the first chamber 21 may be the same as the distribution time. For example, the distribution of A-concentrate is about 15 ml/min, since the volume of a prepared solution is larger than the first chamber 21, the filling rate may be 15 ml/min or a little lower. A lower flow rate decreases the risk of a too large total demand from a source of liquid, such as RO-water In the example of the finished solution being an A-concentrate, the outlet of the device may be connected to a dialysis machine and the concentrate may pass through an exchangeable particle filter. The filter may be arranged in a tube connecting the mixing device with the dialysis machine. The tube may be connected to dialysis machine at the inlet for "central delivery system". There are two main ways a dialysis machine may receive the finished A-concentrate: the dialysis machine uses suction to receive the concentrate from the mixing device; and the pump 25 may be used to pump out the solution to the dialysis machine.

Figure 2E:
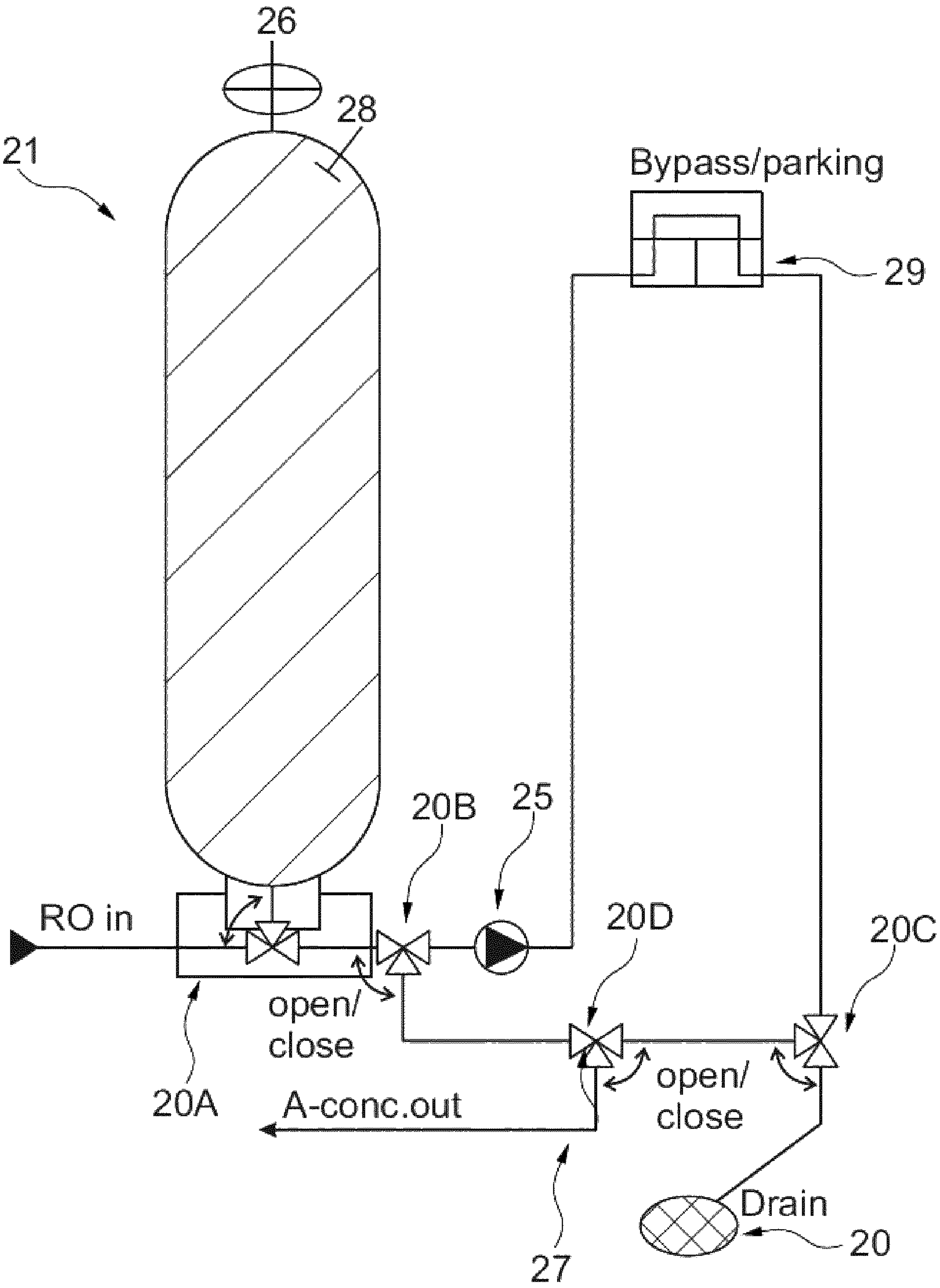

FIG. 2E is illustrating an example of a rinse and drain mode. When the number of batches needed has been prepared, the device needs to be rinsed to remove any residuals. The connector is first arranged in a by-pass mode. How the connector is arranged in a by-pass mode depends on the connector. For some connectors, an adapter is needed to connect the inlet and the out let of the connector. In other examples, the inlet and the outlet can be directly connected to each other to provide a by-pass arrangement.

The solvent, such as RO-water, in the first chamber 21, is pumped, for example by pump 25, through the bypassed connector and through the tubes of the device. Since the first chamber 21 holds a larger volume than the tubes and the bypassed connector. The valves 20B, and 20C may be switched so that 20B is first open, allowing the tube system to fill-up with clean solvent. 20B is closed and the solution is re-circulated by pump 25. Valve 20C is then switched to connect the tubes to the drain 20 and the tubes are emptied, by running the pump 25. This may be repeated until the first chamber 21 is empty. This will rinse the part of the mixing device that has been in contact with the solution and will flush out any residuals of the solvent.

A-concentrate is considered to be sterile and it is therefore not required during normal use to rinse the system with more than RO-water. Sometimes disinfection may be needed, for example if the system may have been exposed to any risk for contamination. For example, if the device has been serviced or repaired; or if not used for a long time. Disinfection may also be needed if the disclosed technology is used for mixing a solution that is not sterile.

The device may be disinfected by connecting a container with a disinfecting solution or powder and then mix it and recirculating the solution in the device before being drained. Alternatively, the inlet may be connected to source of disinfecting solution which is pumped in and recirculated in the device before being drained.

After the device has been disinfected a rinse mode may be run to remove any residuals of the disinfection solution.

Figure 3A:
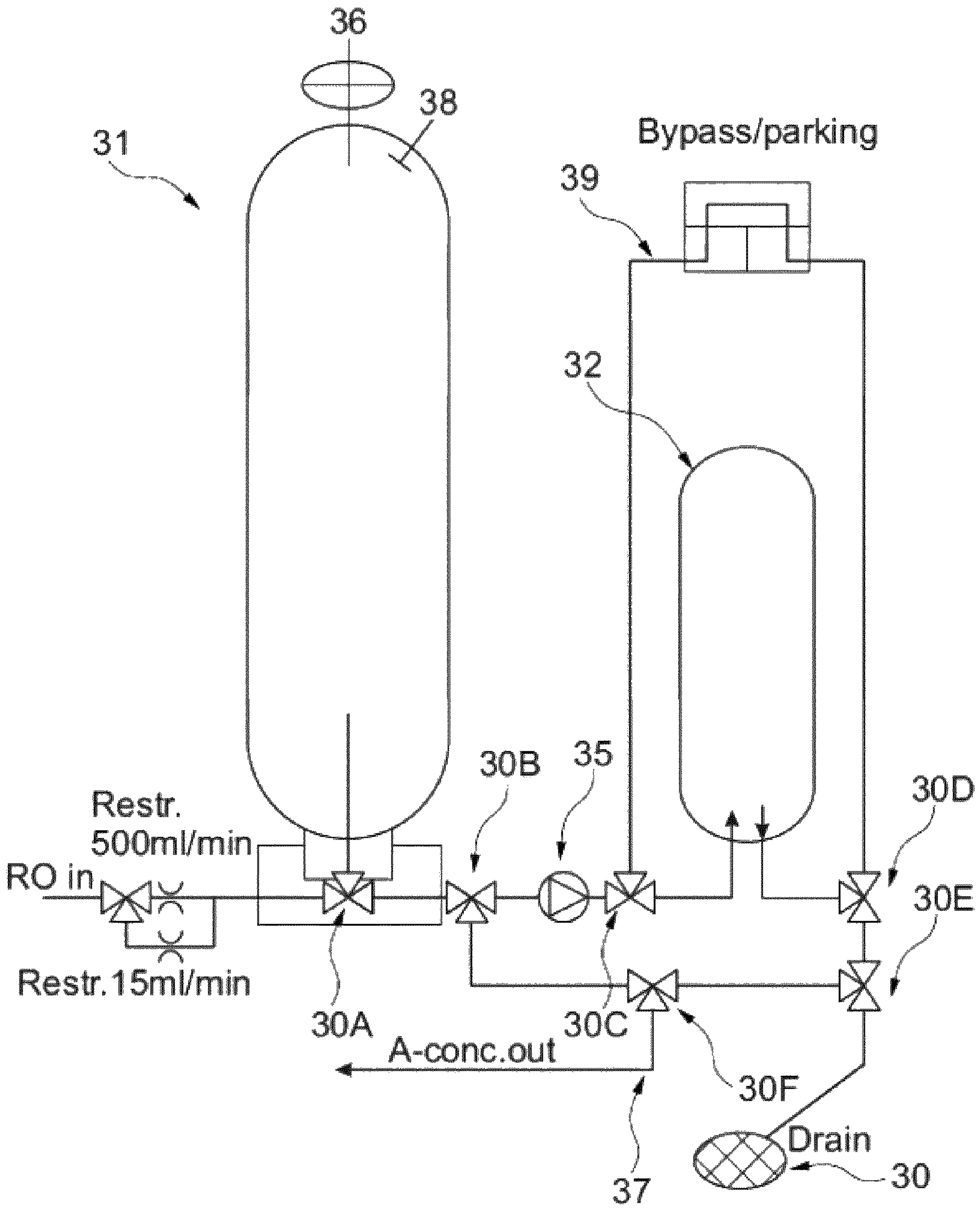
FIGS. 3A-3H are showing a schematic exemplary example of a device for providing a medical solution.

FIGS. 3A to 3H are illustrating a schematic example of a mixing device according to the disclosure. With reference to FIG. 3A, the system includes a first chamber 31, and a second chamber 32. The first chamber 31 having a defined volume for measuring a volume of a liquid, such as a solvent, such as water. The first chamber 31 is connectable through an inlet to a liquid supply, such as a solvent supply, such as a RO-water supply system. The first chamber 31 may include sensor 38, such as a pressure transmitter or pressure sensor. The first chamber 31 may also include a vent 36, such as a breather.

The second chamber 32, comprises an inlet for receiving unsolved solution from the container, and an outlet used for recirculating the solution during mixing. The outlet of the second chamber 32 is also used during distribution of the finished solution and when draining the system during cleaning.

The device may further include some valves, for example, 30A to 30F. Valve 30A is configured for allowing solvent to flow into the first chamber 31 from the supply, such as a RO-water supply system. When the first chamber 31 is filled with solvent, the pressure will increase inside the first chamber 31 whereby the sensor 38 may send a signal to close the valve 30A which stops the filling of the first chamber 31. In this way, the volume of solvent, such as water, will be the same each time when starting the mixture.

Valves, such as valves 30A, 30B and 30C, may be configured to open to allow the solvent to flow out from the first chamber 31 and to the inlet of a connector 39. Emptying the first chamber 31 may be aided by using pump 35. The solvent will be mixed with the content of a container connected to the connector 39. The container includes at least one powder which will be dissolved in the solvent. The mixture flows out from an outlet of the connector 39 via valve 30D to an inlet of the second chamber 32.

After the first chamber 31 and the container has been emptied, valve 30C and 3D close the connection to the outlet and the inlet of the connector 39 and the mixing device is adjusted to facilitate the recirculation of the at least partially unsolved mixture of the at least one powder and the solvent, for example by positioning valves 30B, to 30F so that the pump 35 may re-circulate the mixture from an outlet of the second chamber 32 and through a tube system back to an inlet of the second chamber 32 without the solvent passes through the connector 39.

The recirculation is carried out until a completely saturated solution is obtained from the mixture of solvent and the at least one powder. The finished medical solvent is then distributed through outlet 37, for example via valve 30F. When the finished solution is an A-concentrate for dialysis, the outlet 37 may be connected to an inlet for "Central Delivery System" on the dialysis machine.

The device may also be connectable to a drain 30 when draining and cleaning the mixing system, for example via valve 30E.

The mixing device may include, apart from the chambers, pumps, valves tubes and connectors, also the electronics used for regulating the process and the different sequences of the mixing process.

When the mixing device is configured as a stand-alone machine, the mixing device may also include a display for displaying, for example, start, stop, and the present sequence being carried out. The device may also have an input unit, such as a keyboard or a touch screen.

Some of the Different Modes that the Device May be Perform are:

FIG. 3A is illustrating an example of a standby mode. In this mode, the device is empty and does not include any solvent or finished solution, such as A-concentrate. The device is connected to a solvent supply, such as a water supply, such as RO-water. Valve 30A is in this mode closed. The device may be connected to a machine to which is it distributing the obtainer medical solution, such as connection for delivering A-concentrate on a dialysis machine. Further, the device may be connected to a drain 30.

Figure 3B:
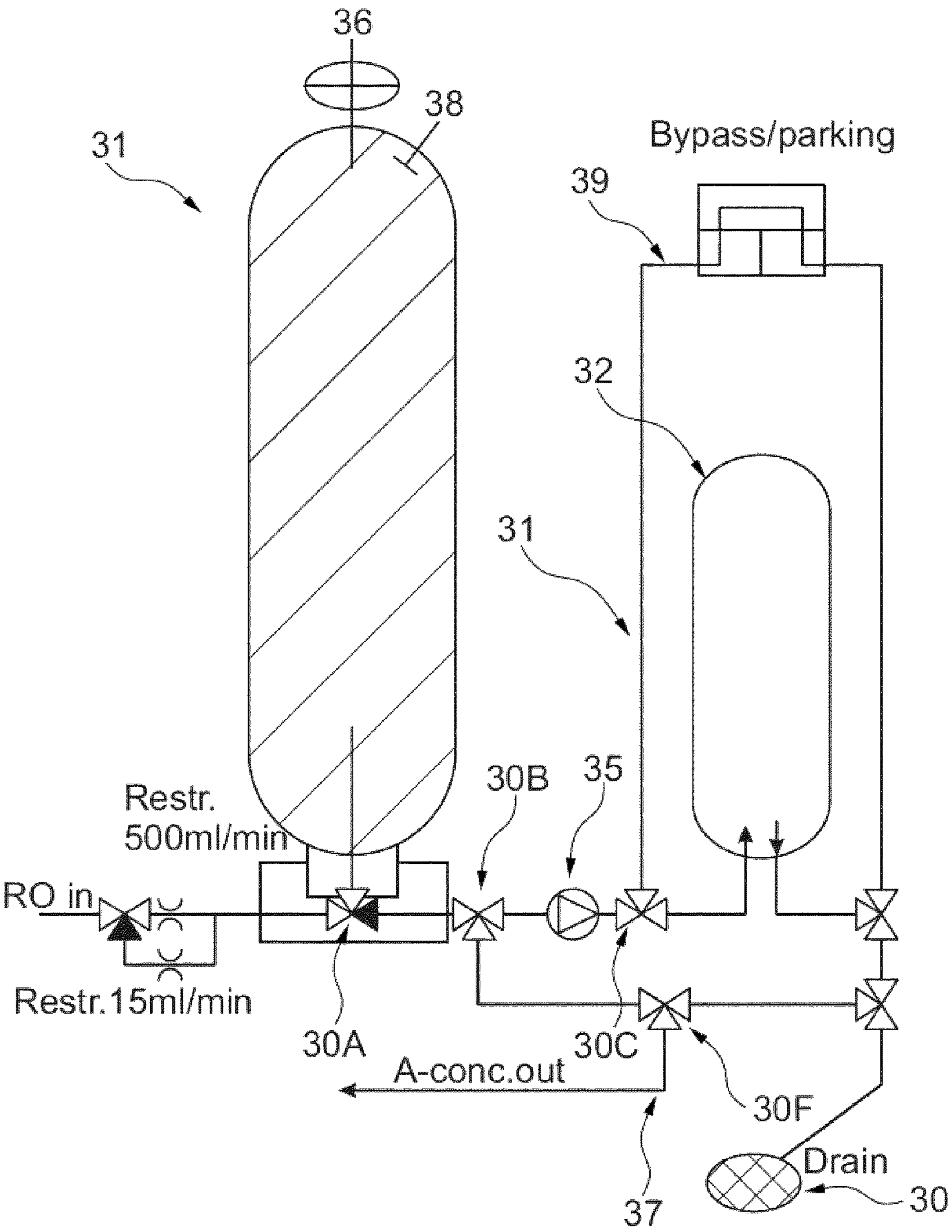

FIG. 3B is illustrating and example of a start-up mode. In this mode, the first chamber 31 is getting filled up with a solvent, such as RO-water, by opening valve 30A. The start-up mode may be initiated by a confirmation, for example, by pushing a button or touching an area on the display. The first chamber 31 is filled until sensor 38 indicates that the first chamber 31 is completely filled with solvent, and whereby valve 30A closes.

When the first chamber 31 is filled with solvent, the pressure will increase inside the first chamber 31 whereby the sensor 38 may send a signal to close the valve 30A which stops the filling of the first chamber 31. In this way, the volume of solvent, such as water, will be the same each time when starting the mixture During start-up mode, a mode of connecting a container may also be performed. The container, such as a bag or cartridge, is connected to the connector 39. When connecting the container to the device, the container may for example be hanged on a stand with the interface of the container to be connected to the connector of the mixing device located at the bottom of the container. Alternatively, the connection interface is arranged at the top of the container, then the solvent may be pumped into the container, but the initial mix of partially unsolved mixture of the at least one powder and the solvent needs to be pumped out from the container, this may be done by pressurizing the container or by suction using, for example, a tube arranged as a straw inside the container.

The disclosure is not limited to a specific type of connector or container. In this application, an example of a connector and container is disclosed, but other connectors and containers known in the art would work, for example, connectors and containers described in EP2723417, EP2035059, and U.S. Pat. No. 6,149,294.

Neither is the disclosure limited to a single container. The system may be adapted so that, for example, two, or three separate containers are connected to the mixing device. For example, where the powders are in a first container, and the acid in a second container; or where the salt and electrolyte is arranged in a first container, the acid in a second container, and the glycose in a third container.

For RO-water, the first time the start-up mode is run, it may be possible to utilize up to the full rate of RO-water delivery. The reason is that the start-up mode may be done at a time of the day when there is not much demand for RO-water. For the consecutive fill-ups of water during a day a restriction to the delivery rate of mixed medicament to a patient, such as about 15 ml/min or lower, may apply.

Figure 3C:
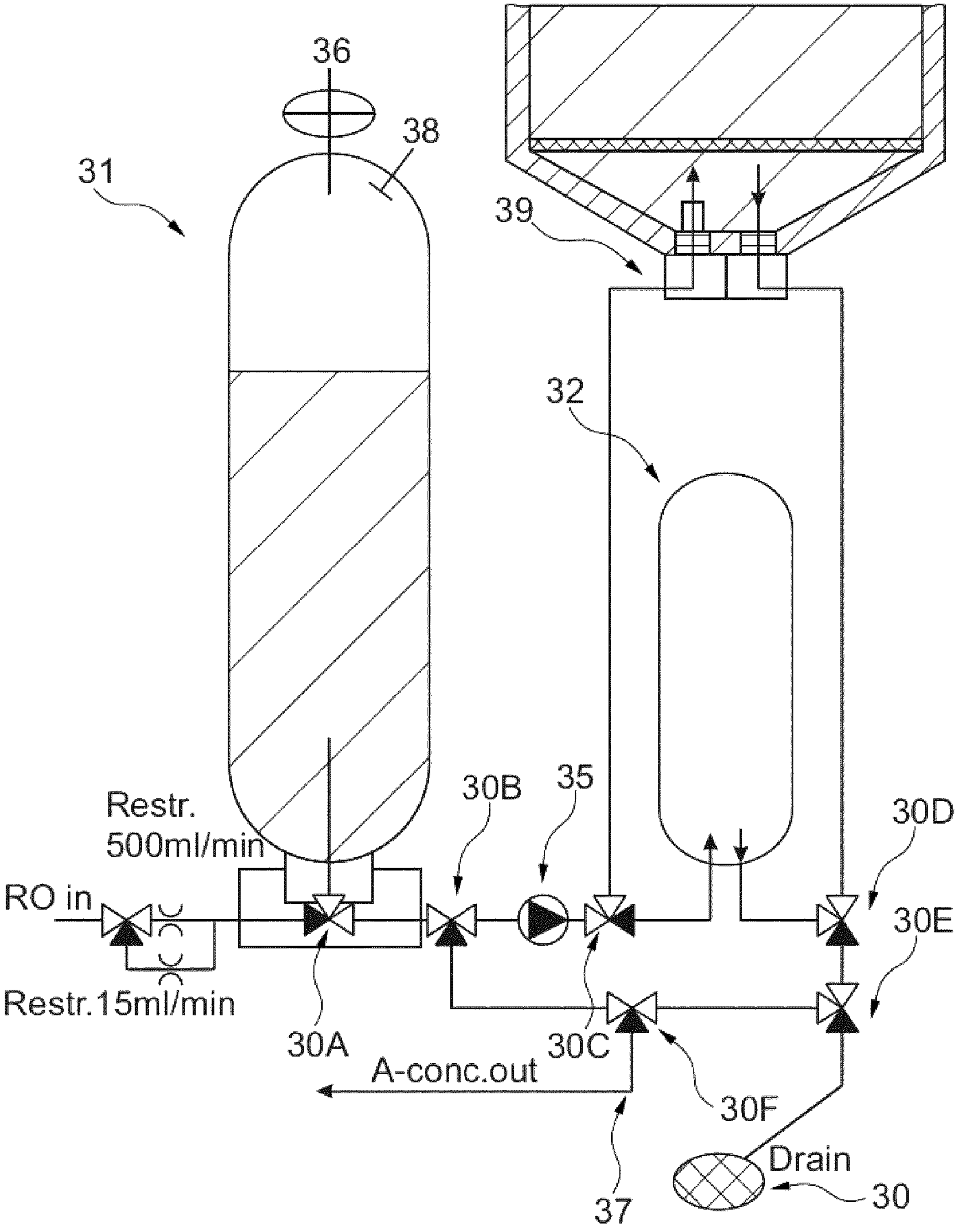

FIG. 3C is illustrating an example of a mode of filling a container. During this mode, pump 35 starts to pump, and the container starts to get filled by a solvent, such as RO-water. Depending on the type of container used, the process may vary. For example, using containers, similar to the containers described in EP2723417, and EP2035059, where there are dividers, such as welded seams, that needs to be opened-up, the outlet of the connector is closed, and a pressure is built up inside the container by the solvent. This may be done by close valve 30D. The increased pressure will break the dividers and allowing the solvent to mix with the content of the container and starting to dissolve the at least one powder therein. In other examples, where separated containers, or a single container having columns wherein each column is separately connected to the connector 39, are used, the solvent fills the container and start to mix with the at least one powder. The content starts to dissolve which allows the bag to be emptied.

Figure 3D:
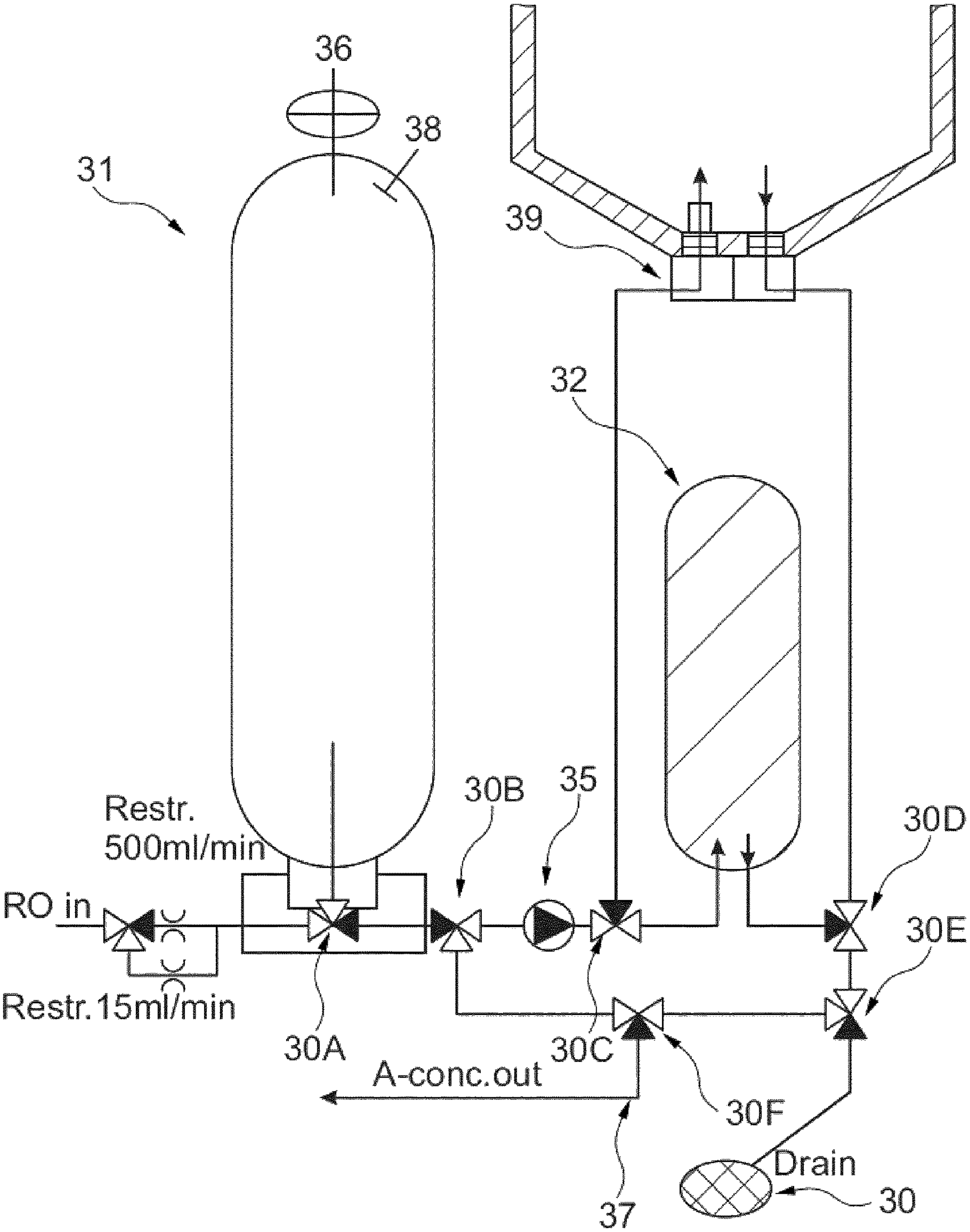

FIG. 3D is illustrating an example of a mode of emptying a container. In this mode, the content of the container is emptied to the second chamber 32 by pump 35 pumping solvent, such as water, from the first chamber 31 and through the container to the inlet of the second chamber 32. Pump 35 is running until the first chamber 31 is empty. When the first chamber 31 is empty, the valve 30C and 30D may close and the container may be replaced according to the "connecting a container mode" described above, and the next "start-up" mode may also be prepared.

Figure 3E:
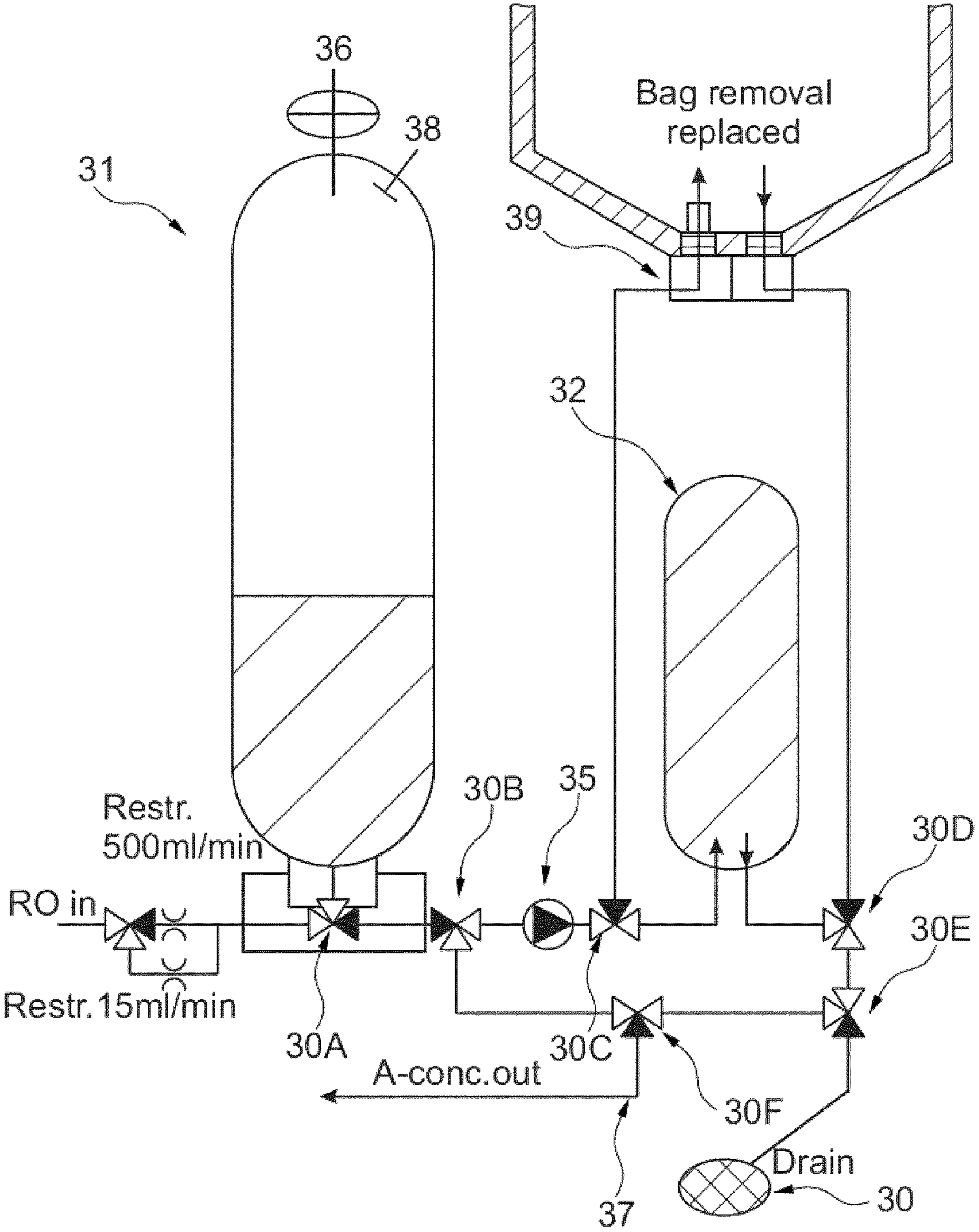

FIG. 3E is illustrating an example of a recirculation mode. When the container has been emptied and the outlet of the connector closed, pump 35, such as a recirculation pump, starts to recirculate the mixture through and inlet and an outlet of the second chamber 32, and tubes connecting them. The recirculation is performed until the mixture is completely saturated and all the powder has been dissolved. The re-circulation may be performed for a defined period of time which is calibrated so that the finished solution will be fully saturated after that defined time or recirculation. When the solution is recirculated, the container may be replaced according to the "connecting a container mode" described above, and the next "start-up" mode may also be running to fill up the first chamber 31 with solvent.

Figure 3F:
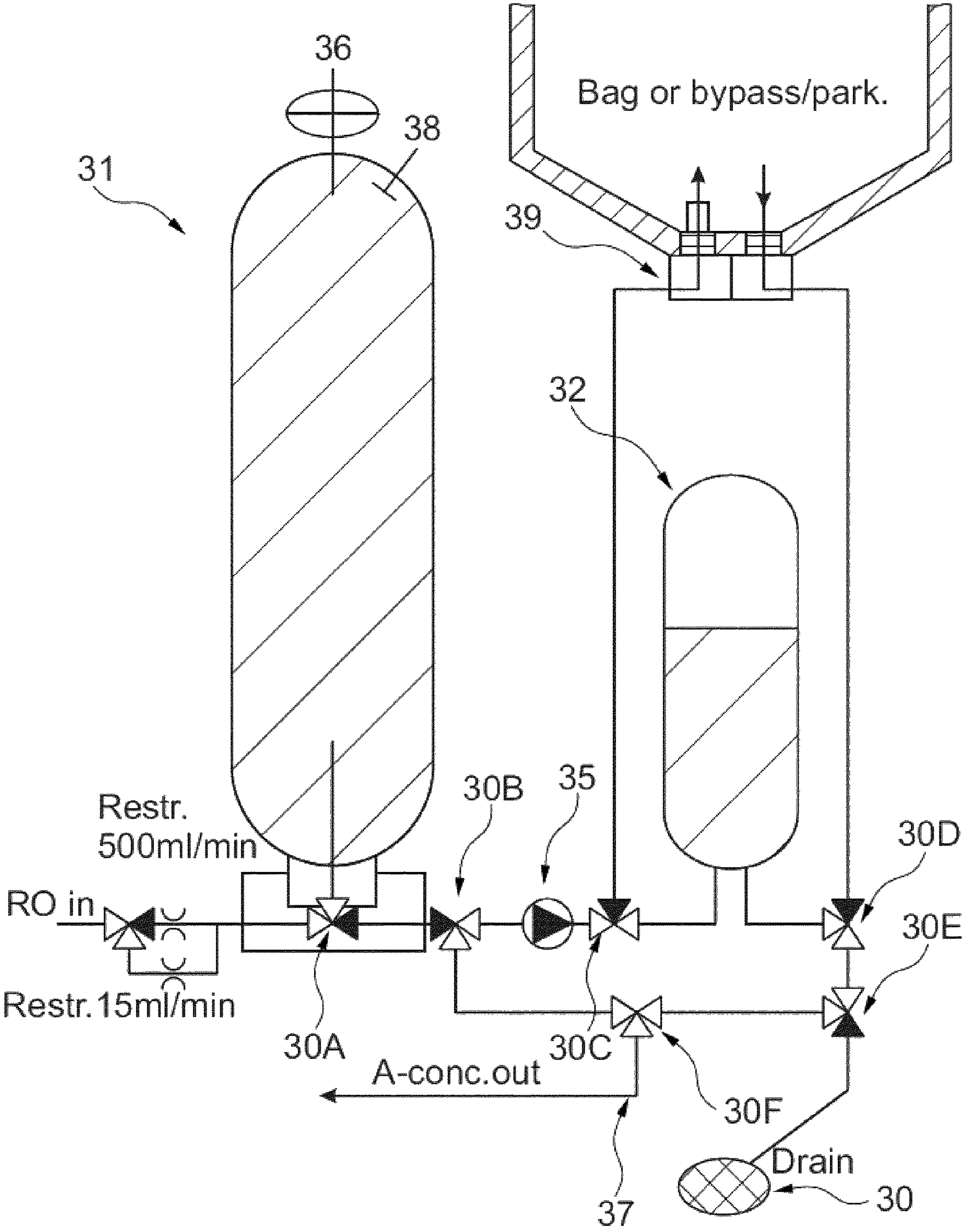

FIG. 3F is illustrating an example of a distribution mode. In this mode is the finished solution distributed, for example through valve 30E. When the finished solution starts to be distributed from the mixing device, the "start-up" mode may be initiated to start to fill the first chamber 31 with a solvent. After the first chamber 31 has been filled, mode for filling the container may be initiated.

The advantages of this is that the machine will be ready to start to mix the solution through recirculation without first filling up the device with water. This allows for a new batch of medical solution to be prepared and started to be distributed within the time for the re-circulation, i.e. for a dialysis patient around 3 min. Another advantage of this arrangement, is that the system allows a longer filling time of solvent. Demanding all the solvent, such as RO-water, needed for the preparation immediately under a short period of time, may cause a high load on a supply system, for example a RO-water supply system. Even about 2 liters of RO-water, which is the normal volume required for a single batch, may cause a too high load if the mixing device must be filled under a short period of time. A high load on a supply system, such as a RO-water supply system, may cause disturbances or in worse case break down the system, so that all units in a clinic may not receive the amount of water they require, which may cause problems for other departments or patents not receiving any water when needed. This may further prolong the preparation of a batch.

If the first chamber 31 may start to get filled during the mixing of a preparation of a solution, the time it may take to fill up the first chamber 31 may be allowed to be longer than when only filing the first chamber 31 during delivery of a preparation. A longer filling time may allow a lower flow rate from a supply system, such as a lower rate than 15 ml/min which is the delivery rate of an A-concentrate to a patient. A lower flow rate decreases the risk of a too large total demand from a source of liquid, such as RO-water.

If the first chamber 31 may start to get filled during the distribution of a prepared solution, the filling time of the first chamber 31 may be the same as the distribution time. For example, the distribution of A-concentrate is about 15 ml/min, since the volume of a prepared solution is larger than the first chamber 31, the filling rate may be 15 ml/min or a little lower. A lower flow rate decreases the risk of a too large total demand from a source of liquid, such as RO-water In the example of the finished solution being an A-concentrate, the outlet of the device may be connected to a dialysis machine and the concentrate may pass through an exchangeable particle filter. The filter may be arranged in a tube connecting the mixing device with the dialysis machine. The tube may be connected to dialysis machine at the inlet for "central delivery system". For this example of a mixing device, there are two main ways a dialysis machine may receive the finished A-concentrate: the dialysis machine uses suction to receive the concentrate from the mixing device; and the recirculation pump 35 is used to pump out the solution to the dialysis machine.

Figure 3G:
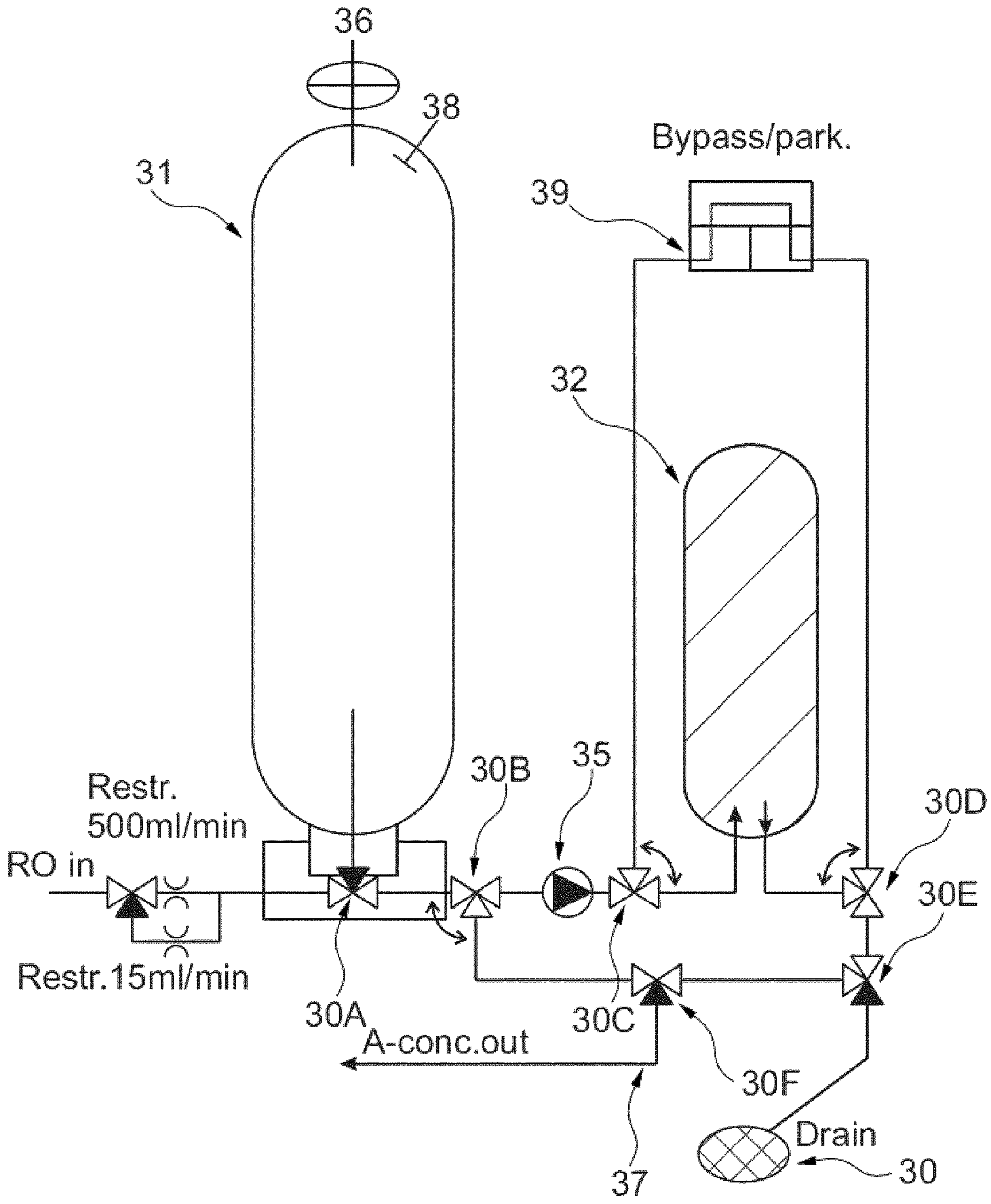

FIG. 3G is illustrating an example of a rinse mode. When the number of batches needed has been prepared, the device needs to be rinsed to remove any residuals. The connector is first arranged in a by-pass mode. How the connector is arranged in a by-pass mode depends on the connector. For some connectors, an adapter is needed to connect the inlet and the out let of the connector. In other examples, the inlet and the outlet can be directly connected to each other to provide a by-pass arrangement.

The rinsing may be done by the solvent, such as RO-water, in the first chamber 31, being pumped, for example by pump 35, through the bypassed connector and into the second chamber 32. When the first chamber 31 is empty, the recirculation pump 35 starts to recirculate the solvent through the inlet and the outlet of the second chamber 32 and the tubes connecting them. This will rinse the part of the mixing device that has been in contact with the solution and will flush out any residuals of the solvent.

Alternatively, and/or additionally, the solvent for rinsing the system may be received directly from the supply source, such as the RO-water supply (as illustrated).

A-concentrate is considered to be sterile and it is therefore not required during normal use to rinse the system with more than RO-water. Sometimes disinfection may be needed, for example if the system may have been exposed to any risk for contamination. For example, if the device has been serviced or repaired; or if not used for a long time. Disinfection may also be needed if the disclosed technology is used for mixing a solution that is not sterile.

The device may be disinfected by connecting a container with a disinfecting solution or powder and then mix it and recirculating the solution in the device before being drained. Alternatively, the inlet may be connected to source of disinfecting solution which is pumped in and recirculated in the device before being drained.

After the device has been disinfected a rinse mode may be run to remove any residuals of the disinfection solution.

Figure 3H:
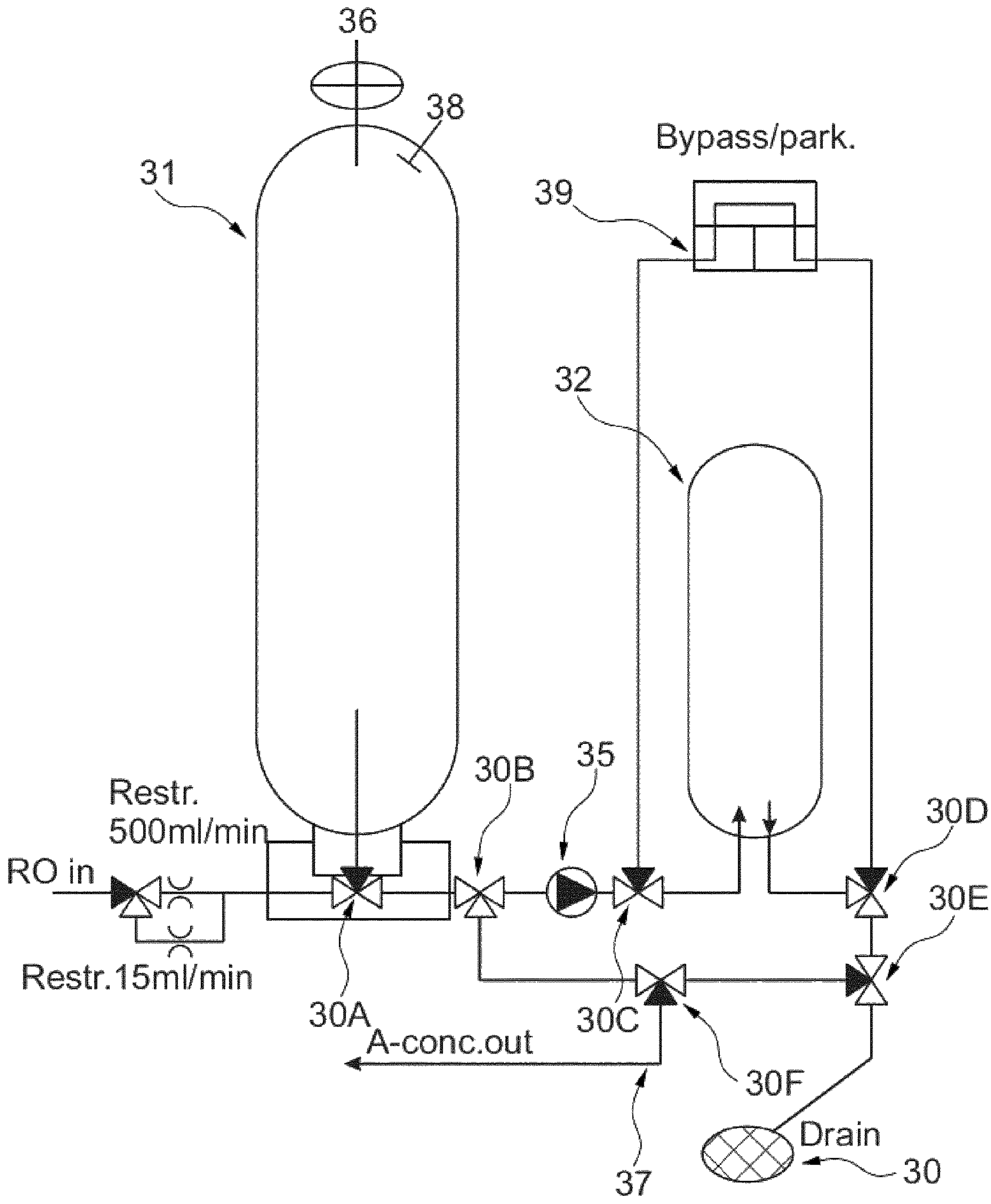

FIG. 3H is illustrating an example of a drain mode. When the device has been rinsed, the solvent used for rinsing the device is emptied into a drain 30, such as by open valve 30E.

The rinse mode and drain mode may be repeated should so be needed. A special rinsing liquid may also be used for this process.

In this mode, the pump 35 may be used to pump out the solvent used for the rinse. Alternatively, the solvent used for the rinse may be drained without the use of pump 35, for example by gravity or by suction from the drain 30.

The present invention has been described above with reference to specific embodiments. However, other embodiments than the above described are equally possible within the scope of the invention. Different method steps than those described above, performing the method by hardware or software, may be provided within the scope of the invention. The different features and steps of the invention may be combined in other combinations than those described. The scope of the invention is only limited by the appended patent claims.

The invention claimed is:

1. A device for providing a medical solution, the device comprising:

a first chamber adapted to have a defined volume, the first chamber is configured to be connected to a liquid providing system to fill the first chamber with the defined volume of liquid;

a connector for connecting a container including at least one powder, wherein the connector has an inlet and an outlet;

a channel connecting the first chamber with the inlet of the connector; and an outlet for distributing the medical solution;

wherein the device is configured to mix the at least one powder with the defined volume of liquid for a period of time, and wherein the device is configured to fill the first chamber with the liquid from the liquid providing system while mixing the medical solution and/or distributing the mixed medical solution through the outlet; and a second chamber adapted to have a volume larger than the first chamber, wherein the second chamber comprises an inlet and an outlet, the inlet of the second chamber is connected to the outlet of the connector for transferring a mixture comprising the at least one powder and the volume of liquid from the container to the second chamber, and the outlet of the second chamber is connected to the outlet for distributing the medical solution;

wherein the second chamber is configured for mixing the mixture for the period of time by recirculation through the inlet and the outlet of the second chamber.

2. The device of claim 1, wherein the device comprises a re-circulation pump for mixing the powder and liquid by recirculation.

3. The device of claim 1, wherein the first chamber and the second chamber are separated by a flexible or movable wall.

4. The device of claim 3, wherein the second chamber comprises two parts, a first part and a second part, the first part has the same volume as the first chamber and is defined by the flexible or movable wall and a fixed wall being perforated, the second part is connected to the perforated wall to provide a larger volume to the second chamber compared to the first chamber.

5. A dialysis machine which comprises a device according to claim 1 for providing an A-concentrate.

6. A method of providing a medical solution, comprising:

filling a first chamber having a defined volume with a liquid to obtain a defined volume of liquid;

connecting a container including at least one powder to a connector having and inlet and an outlet;

introducing the liquid from the first chamber to the container through the inlet of the connector;

mixing the at least one powder with the defined volume of liquid for a period of time by recirculation;

distributing the medical solution through a distribution outlet, wherein the first chamber is being filled with liquid while mixing the medical solution and/or distributing the mixed medical solution through the distribution outlet; and pumping a mixture comprising the at least one powder and the defined volume of liquid from the container to a second chamber, through the outlet of the connector to an inlet of the second chamber; and mixing the mixture for the period of time by recirculation the mixture through the inlet and an outlet of the second chamber;

wherein the outlet of the second chamber is connected to the distribution outlet.

7. The method of claim 6, wherein the medical solution is an A-concentrate, and the distribution outlet is connected to a dialysis machine.

* * * * *